(12) United States Patent
Layzell et al.

(10) Patent No.: US 12,343,327 B2
(45) Date of Patent: *Jul. 1, 2025

(54) INJECTABLE FORMULATIONS

(71) Applicant: CYBIN UK LTD, London (GB)

(72) Inventors: Marie Claire Layzell, London (GB); James Maxwell Rennie, London (GB)

(73) Assignee: Cybin UK Ltd, London (GB)

(*) Notice: Subject to any disclaimer, the term of this patent is extended or adjusted under 35 U.S.C. 154(b) by 317 days.

This patent is subject to a terminal disclaimer.

(21) Appl. No.: 17/806,526

(22) Filed: Jun. 13, 2022

(65) Prior Publication Data

US 2022/0313660 A1    Oct. 6, 2022

Related U.S. Application Data

(63) Continuation of application No. 17/459,284, filed on Aug. 27, 2021, now Pat. No. 11,406,619, which is a continuation-in-part of application No. 17/006,115, filed on Aug. 28, 2020, now abandoned.

(30) Foreign Application Priority Data

Aug. 28, 2020 (GB) ........................ 2013571

(51) Int. Cl.
*A61K 31/4045* (2006.01)
*A61K 47/02* (2006.01)
*A61K 47/12* (2006.01)

(52) U.S. Cl.
CPC .......... *A61K 31/4045* (2013.01); *A61K 47/02* (2013.01); *A61K 47/12* (2013.01)

(58) Field of Classification Search
CPC .................... A61K 31/4045; A61K 9/0019
See application file for complete search history.

(56) References Cited

U.S. PATENT DOCUMENTS

| | | | |
|---|---|---|---|
| 4,336,378 A | 6/1982 | Brand et al. | |
| 8,268,856 B2 | 9/2012 | Hamann et al. | |
| 11,000,534 B1 | 5/2021 | Sippy | |
| 11,242,318 B2 | 2/2022 | Nivorozhkin et al. | |
| 11,406,619 B2 | 8/2022 | Layzell et al. | |
| 11,471,417 B2 | 10/2022 | Rands et al. | |
| 11,578,039 B2 | 2/2023 | Rands et al. | |
| 11,643,390 B2 | 5/2023 | Rands et al. | |
| 11,660,289 B2 | 5/2023 | Rands et al. | |
| 11,697,638 B2 | 7/2023 | Rands et al. | |
| 11,773,062 B2 | 10/2023 | Rands et al. | |
| 2002/0022667 A1 | 2/2002 | Pace et al. | |
| 2009/0076121 A1 | 3/2009 | Czarnik | |
| 2013/0129812 A1* | 5/2013 | Ozpolat .................. | A61P 35/00 514/415 |
| 2018/0221396 A1 | 8/2018 | Chadeayne | |
| 2020/0339519 A1 | 10/2020 | Kim et al. | |
| 2020/0390746 A1 | 12/2020 | Rands et al. | |
| 2021/0378969 A1 | 12/2021 | Rands et al. | |
| 2021/0395201 A1 | 12/2021 | Rands et al. | |
| 2021/0403426 A1 | 12/2021 | Rands et al. | |
| 2022/0062237 A1 | 3/2022 | Layzell et al. | |
| 2022/0062238 A1 | 3/2022 | Layzell et al. | |
| 2022/0081396 A1 | 3/2022 | Rands et al. | |
| 2022/0168275 A1 | 6/2022 | Rands et al. | |
| 2022/0202775 A1 | 6/2022 | Rands et al. | |
| 2022/0281818 A1 | 9/2022 | Rands et al. | |
| 2023/0086574 A1 | 3/2023 | Rands et al. | |
| 2023/0149293 A1 | 5/2023 | Rands et al. | |
| 2023/0167056 A1 | 6/2023 | Rands et al. | |
| 2023/0181530 A1 | 6/2023 | Rands et al. | |
| 2023/0250059 A1 | 8/2023 | Rands et al. | |
| 2024/0016782 A1 | 1/2024 | Rands et al. | |
| 2024/0217929 A1 | 7/2024 | Rands et al. | |
| 2024/0325351 A1 | 10/2024 | Rands et al. | |

FOREIGN PATENT DOCUMENTS

| | | |
|---|---|---|
| GB | 2585978 A | 1/2021 |
| GB | 2586940 A | 3/2021 |
| GB | 2596884 A | 1/2022 |
| WO | 02083144 A1 | 10/2002 |
| WO | 2004085392 A1 | 10/2004 |
| WO | 2008049116 A2 | 4/2008 |
| WO | 2008071455 A1 | 6/2008 |
| WO | 2009049030 A1 | 4/2009 |
| WO | 2009087682 A2 | 7/2009 |

(Continued)

OTHER PUBLICATIONS

Avis, "Chapter 84: Parental Preparations" in Remington's Pharmaceutical Sciences, pp. 1545-1569, 18th Ed., Mack Printing Company, Easton, Pennsylvania, USA. 1990.
Broadhead, "Chapter 9: Parental Dosage Forms" in Pharmaceutical Preformulation and Formulation: A practical Fuide from Candidate Drug Selection to Commercial Dosage Form, pp. 325-347, 2nd Ed., vol. 199, Informa Healthcare, New York, New York, USA. 2009.
Butler et al., "Removal of Dissolved Oxygen from Water: A Comparison of Four Common Techniques", Talanta, vol. 41, No. 2, pp. 211-215. 1994.
Connors et al., "Chapter 5: Oxidation" in Chemical Stability of Pharmaceuticals: A Handbook for Pharmacists, pp. 80-98, John Wiley & Sons, New York, USA. 1979.
Cozzi et al., "Synthesis and Characterization of High-Purity N,N-Dimethyltryptamine Hemifumarate for Human Clinical Trials", Drug Test Anal., vol. 12, pp. 1483-1493. 2020.
Human Metabolome Database, Showing Metabocard for Dimethyltryptamine (HMDB0005973), 6 pages, Updated Feb. 26, 2020.
Imitrex Product Insert, Highlights of Prescribing Information, 35 pages, revised Nov. 2015.

(Continued)

*Primary Examiner* — San Ming R Hui
(74) *Attorney, Agent, or Firm* — Heslin Rothenberg Farley & Mesiti P.C.

(57) ABSTRACT

Provided herein are pharmaceutical formulations, methods for their production, and uses thereof. The pharmaceutical formulations comprise a salt of an optionally substituted dimethyltryptamine compound, a buffer, which is separate to the salt, and water. The formulations have pH values of from about 3.5 to about 6.5 and osmolalities of about 250 to about 350 mOsm/Kg. Such formulations are suitable for injection, being both stable and clinically acceptable, and have potential uses in the treatment of psychiatric or neurological disorders.

19 Claims, No Drawings

(56) References Cited

FOREIGN PATENT DOCUMENTS

| WO | 2009133455 A2 | 11/2009 |
|---|---|---|
| WO | 2018195455 A1 | 10/2018 |
| WO | 2019081764 A1 | 5/2019 |
| WO | 2020136466 A1 | 7/2020 |
| WO | 2020169850 A1 | 8/2020 |
| WO | 2020169851 A1 | 8/2020 |
| WO | 2020176597 A1 | 9/2020 |
| WO | 2020176599 A1 | 9/2020 |
| WO | 2020245133 A1 | 12/2020 |
| WO | 2021089872 A1 | 5/2021 |
| WO | 2021089873 A1 | 5/2021 |
| WO | 2021116503 A2 | 6/2021 |
| WO | 2021155470 A1 | 8/2021 |
| WO | 2021234608 A1 | 11/2021 |
| WO | 2021244831 A1 | 12/2021 |
| WO | 2022011350 A1 | 1/2022 |
| WO | 2022031566 A1 | 2/2022 |
| WO | 2022043227 A1 | 3/2022 |
| WO | 2022069690 A2 | 4/2022 |
| WO | 2022082058 A1 | 4/2022 |
| WO | 2022117359 A1 | 6/2022 |

OTHER PUBLICATIONS

Budavari et al. The Merck Index, Print Version, Twelfth Edition: An encyclopedia of chemicals, drugs, and biologicals, 1 page. 1996.
Strassman et al., "Differential Tolerance to Biological and Subjective Effects of Four Closely Spaced Doses of N, N-Dimethyltryptamine in Humans", Biol. Psychiatry, vol. 39, pp. 784-795. 1996.
Timmermann et al., "Neural Correlates of the DMT Experience Assessed with Multivariate EEG", Scientific Reports, Nature Research, vol. 9, 13 pages. 2019.
Uthaug et al., "A Comparison of Reactivation Experiences Following Vaporization and Intramuscular Injection (IM) of Synthetic 5-Methoxy-N,N-Dimethyltryptamine (5-MeO-DMT) in a Naturalistic Setting", Journal of Psychedelic Studies, vol. 4, No. 2, pp. 104-113. 2020.
Waterman et al., "Stabilization of Pharmaceuticals to Oxidative Degradation" Pharmaceutical Development and Technology, vol. 7(1), pp. 1-32. 2002.
ABB, "Freeze drying in the pharmaceutical industry" (https://new.abb.com/control-systems/industry-specific-solutions/pharmaceutical-and-life-sciences/freeze-drying-in-the-pharmaceutical-industry; accessed Feb. 9, 2023, archived via WayBack Machine; 4 pages. 2017.
Cai, "Monamine oxidase inhibitors: Promising therapeutic agents for Alzheimer's disease", Molecular Medicine Reports, 9(5), pp. 1533-1541. 2014.
Carbonaro et al., Neuropharmacology of N, N-Dimethyltryptamine, Brain Res Bull, 126, pp. 74-88. 2016.
Hopkins et al., "Large-volume IM injections: A review of best practices", https://www.oncologynurseadvisor.com/home/hot-topics/chemotherapy/large-volume-im-injections-a-review-of-best-practices/; accessed Feb. 9, 2023, pp. 32-37. Feb. 2013.
Millrock Technology "What is Lyophilization?" (https://www.millrocktech.com/lyosight/lyobrary/what-is-lyophilization/; accessed Feb. 9, 2023, 2 pages. 2023.
Reiff et al., "Psychedelics and Psychedelic-Assisted Psychotherapy", Am J. Psychiatry, 177:5, pp. 391-410. May 2020.
Barker et al., "Metabolism of the Hallucinogen N,N-Dimethyltryptamine in Rat Brain Homogenates", Biochemical Pharmacology, vol. 29, pp. 1049-1057. 1980.
Rands et al., Unpublished U.S. Appl. No. 18/193,866, filed Mar. 31, 2023.
Rands et al., Unpublished U.S. Appl. No. 18/152,465, filed Jan. 10, 2023.
Rands et al., Unpublished U.S. Appl. No. 18/056,771, filed Nov. 18, 2022.
Rands et al., Unpublished U.S. Appl. No. 18/163,388, filed Feb. 2, 2023.

Atzrodt et al. Deuterium- and Tritium-Labelled Compounds: Applications in the Life Sciences, Angew. Chem. Int. Ed., vol. 57, pp. 1758-1784. 2018.
U.S. Appl. No. 18/252,949 to Rands et al. May 15, 2023.
Kazakevich et al., "HPLC For Pharmaceutical Scientists", Chapters 14 and 21, 71 pages. May 16, 2006.
Andersen et al., "Therapeutic Effects of Classic Serotonergic Psychedelics: A Systematic Review of Modern-Era Clinical Studies", Acta Psychiatrica Scandinavica, vol. 143, pp. 101-118. 2021.
Pires et al., "Gas Chromatographic Analysis of Dimethyltryptamine and ß-Carboline Alkaloids in Ayahuasca, an Amazonian Psychoactive Plant Beverage", Phytochemical Analysis, vol. 20, pp. 149-153. Jan. 12, 2009.
Silveira et al., "Stability Evaluation of DMT and Harmala Alkaloids in Ayahuasca Tea Samples", Molecules, vol. 25, 11 pages. 2020.
Roseman et al., "Quality of Acute Psychedelic Experience Predicts Therapeutic Efficacy of Psilocybin for Treatment-Resistant Depression", Frontiers in Pharmacology, vol. 8, Article 974, 10 pages. Jan. 2018.
Ambinter Screening Library, CAS Registry No. 1794811-18-9, Order No. Cat. Amb33838664 Mar. 26, 2020.
Aurora Building Blocks 2, CAS Registry No. 1435934-64-7, Order No. Cat A17.921.638. Feb. 27, 2020.
MuseChem Product List, CAS Registry No. 1794756-39-0, Order No. Cat. R055190. Apr. 21, 2020.
Barker, et al., "Comparison of the Brain Levels of N N-Dimethyltryptamine and a,a,B,B-Tetradeutero N, N-Dimethyltryptamine Following Intraperitoneal Injection", Biochemical Pharmacology, vol. 31, No. 15, pp. 2513-2516 Jan. 20, 1982.
Barker, Steven A., "N, N-Dimethyltryptamine (DMT), an Endogenous Hallucinogen: Past, Present, and Future Research to Determine Its Role and Function", Frontiers in Neuroscience, vol. 12, Article 536, pp. 1-17 Aug. 6, 2018.
Beaton, et al., "A Comparison of the Behavioral Effects of Proteo- and Deutero-N, N-Dimethyltryptamine", Pharmacology, Biochemistry & Behavior, vol. 16, pp. 811-814 Sep. 8, 1982.
Brandt, et al., "Microwave-Accelerated Synthesis of Psychoactive Deuterated N, N-Dialkylated-[a, a, ?, ?-d4]-Tryptamines", Journal of Labelled Compounds and Radiopharmaceuticals, vol. 51, No. 14, pp. 423-429 Nov. 1, 2008.
Cameron, et el., "Effects of N,N-Dimethyltryptamine on Rat Behaviors Relevant to Anxiety and Depression", ACS Chemical Neuroscience, vol. 9, No. 7, pp. 1582-1590 2018.
Celik, et al., "Binding of Serotonin to the Human Serotonin Transporter. Molecular Modeling and Experimental Validation" Journal of the American Chemical Society, vol. 130, No. 12, pp. 3853-3865 Mar. 2008.
Celik, et al., "Supplementary Information to Binding of Serotonin to the Human Serotonin Transporter. Molecular Modeling and Experimental Validation", Journal of the American Chemical Society, 14 pages Mar. 2008.
Chemieliva Pharmaceutical Product, CAS Registry No. 1794811-18-9, "Supplementary Disclosures", Chemieliva Pharmaceutical Product List, Order No. Cat. CC0034141 Jan. 28, 2021.
Chemieliva Pharmaceutical Product, CAS Registry No. 1794756-39-0, "Supplementary Disclosures", Chemieliva Pharmaceutical Product List, Order No. Cat. CC0034145 Jan. 28, 2021.
Dunlap et al., "Identification of Psychoplastogenic N,N-Dimethylaminoisotryptamine (isoDMT) Analogues through Structure—Activity Relationship Studies", Journal of Medicinal Chemistry, vol. 63, pp. 1142-1155 2020.
Dyck, et al., "Effect of Deuterium Substitution on the Disposition of Intraperitoneal Tryptamine", Biochemical Pharmacology, vol. 35, No. 17, pp. 2893-2896 1986.
Gaujac, et al., Investigations into the polymorphic properties of N,N-dimethyltryptamine by X-ray diffraction and differential scanning calorimetry, Microchemical Journal, vol. 110, pp. 146-157 2013.
Ghosal, et al., "Indole Bases of Desmodium Gyrans", Phytochemistry (Elsevier), vol. 11, No. 5, pp. 1863-1864 1972.
Grina, et al., "Old and New Alkaloids From Zanthoxylum Arborescens", Journal of Organic Chemistry, vol. 47, No. 13, pp. 2648-2651 1982.

(56) References Cited

OTHER PUBLICATIONS

Halberstadt, et al., "Behavorial effects of α,α,β,β-tetradeutero-5-MeO-DMT in rats: comparison with 5-MeO-DMT administered in combination with a monoamine oxidase inhibitor", Psychopharmacology, vol. 221, pp. 709-718. Jan. 6, 2012.
Ibrahim, et al., "Marine inspired 2-(5-Halo-1 H-indol-3-yl)-N,N-dimethylethanamines as Modulators of Serotonin Receptors: An Example Illustrating the Power of Bromine as Part of the Uniquely Marine Chemical Space", Marine drugs, vol. 15, No. (8), pp. 248/1-248/14 2017.
Mcilhenny, et al., "Direct Analysis of Psychoactive Tryptamine and Harmala Alkaloids in the Amazonian Botanical Medicine Ayahuasca by Liquid Chromatography-electrospray Ionization-tandem Mass Spectrometry", Journal of Chromatography A, vol. 1216, No. 51, 9 pages. 2009.
Morris, et al., "Indolealkylamine Metabolism: Synthesis of Deuterated Indolealkylamines as Metabolic Probes", Journal of Labelled Compounds and Radiopharmaceuticals, John Wiley & Sons Ltd., vol. 33, No. 6, pp. 455-465 1993.
Queiroz, et al., "Chemical Composition of the Bark of Tetrapterys Mucronata and Identification of Acetylcholinesterase Inhibitory Constituents", Journal of Natural Products, vol. 77, No. 3, 2014, pp. 650-656 2014.
Riga, et al., The serotonin hallucinogen 5-MeO-DMT alters corticothalamic activity in freely moving mice: Regionally-selective involvement of 5-HT1A and 5-HT2A receptors, Neuropharmacology, vol. 142, pp. 219-230 2017.
Sard, et al., "SAR of psilocybin analogs: Discovery of a selective 5-HT2c agonist", Bioorganic & Medicinal Chemistry Letters 15, vol. 15, No. 20, pp. 4555-4559 2005.
Servillo, et al., "Citrus Genus Plants Contain N-Methylated Tryptamine Derivatives and Their 5-Hydroxylated Forms", Journal of Agricultural and Food Chemistry, vol. 61, No. 21, pp. 5156-5162 2013.
Strassman et al., "Dose-Response Study of N, N-Dimethyltryptamine in Humans: II. Subjective Effects and Preliminary Results of a New Rating Scale", Archives of General Psychiatry, Chicago, IL, vol. 51(2), pp. 98-108 Feb. 1994.
Tearavarich et al. "Microwave-Accelerated Preparation and Analytical Characterization of 5-ethoxy-N,N-dialkyl-[α,α,β,β-H4]- and [α,α,β,β-D4]-tryptamines", Drug Testing and Analysis, vol. 3, No. 9, pp. 597-608 Dec. 2010.
Walker, et al., "Gas Chromatographic-Mass Spectrometric Isotope Dilution Assay for N,N-Dimethyltryptamine in Human Plasma", Biochemical Medicine, vol. 8, pp. 105-113 1973.
Timmins, Expert Opin Ther Pat., 24(10), pp. 1067-1075. Oct. 2014.
Rands et al., Unpublished U.S. Appl. No. 17/616,345, filed Dec. 3, 2021.
Rands et al., Unpublished U.S. Appl. No. 17/469,063, filed Sep. 8, 2021.
Rands et al., Unpublished U.S. Appl. No. 17/574,424, filed Jan. 12, 2022.
Rands et al., Unpublished U.S. Appl. No. 17/680,411, filed Feb. 25, 2022.
Brito-Da-Costa et al. "Toxicokinetics and Toxicodynamics of Ayahuasca Alkaloids N,N-Dimethyltryptamine (DMT), Harmine, Harmaline and Tetrahydroharmine: Clinical and Forensic Impact", Pharmaceuticals, vol. 13, No. 334, 36 pages. Oct. 23, 2020.
Usach et al., "Subcutaneous Injection of Drugs: Literature Review of Factors Influencing Pain Sensation at the Injection Site", Adv. Ther., vol. 36, pp. 2986-2996. Only Cite in 006A Oct. 5, 2019.
Rands et al., Unpublished U.S. Appl. No. 18/602,171, filed Mar. 12, 2024.
WANG "Tolerability of Hypertonic Injectables" International Journal of Pharmaceutics, 490. 2015.
Rands et al., Unpublished U.S. Appl. No. 18/711,130, filed May 17, 2024.
Rands et al. Unpublished U.S. Appl. No. 18/619,547, filed Mar. 28, 2024.

\* cited by examiner

INJECTABLE FORMULATIONS

CROSS-REFERENCE TO RELATED APPLICATIONS

This application is a continuation of U.S. patent application Ser. No. 17/459,284 filed Aug. 27, 2021, which is a continuation in part of U.S. patent application Ser. No. 17/006,115, filed Aug. 28, 2020, and claims benefit to United Kingdom Application No. 2013571.1, filed Aug. 28, 2020, the entire disclosures of each of which are incorporated by reference herein.

BACKGROUND

Classical psychedelics have shown preclinical and clinical promise in treating psychiatric disorders (Carhart-Harris and Goodwin, *Neuropsychopharmacology* 42, 2105-2113 (2017)). In particular, psilocybin has demonstrated significant improvement in a range of depression and anxiety rating scales in randomised double blind studies (Griffiths et al. *Journal of Psychopharmacology*, 30 (12), 1181-1197 (2016)).

N,N-dimethyltryptamine (DMT) is also understood to hold therapeutic value as a short-acting psychedelic. A review of research into the biosynthesis and metabolism of DMT in the brain and peripheral tissues, methods and results for DMT detection in body fluids and the brain, new sites of action for DMT, and new data regarding the possible physiological and therapeutic roles of DMT is provided by S. A. Barker in *Front. Neurosci.*, 12, 536, 1-17 (2018). In this review, DMT is described as having a possible therapeutic role in the treatment of depression, obsessive-compulsive disorder, and substance abuse disorders.

The injection of saline solutions of DMT fumarate salts into human volunteers is described in C. Timmermann et al., *Sci. Rep.*, 9, 16324 (2019). The effect of DMT fumarate on the power spectrum and signal diversity of human brain activity was recorded via multivariate EEG and compared with the results obtained on injection of a placebo (saline solution). It was found that, relative to the results obtained with the placebo, DMT fumarate suppressed alpha power and normalized/increased delta and theta power. Alpha power has been linked with high-level psychological functioning, top-down predictive processing and related feedback connectivity, whilst theta and delta power is classically associated with REM sleep dreaming and related 'visionary' states. It is described that these results relate injection of DMT fumarate to the experience of feeling profoundly immersed in an entirely other world.

According to the Human Metabolome Database (HMDB), dimethyltryptamine degrades relatively quickly in solution (see specifically http://www.hmdb.ca/metabolites/HMDB0005973). Consequently, there is a need in the art for injectable solutions of DMT that are stable over longer periods of time, and are clinically acceptable. The present invention addresses this need.

SUMMARY

The present invention relates to pharmaceutical formulations, methods for their production, and uses thereof. The pharmaceutical formulations comprise a salt of an optionally substituted dimethyltryptamine compound, a buffer, which is separate to the salt, and water. The formulations have pH values of from about 3.5 to about 6.5 and osmolalities of about 250 to about 350 mOsm/Kg. Such formulations are suitable for injection, being both stable and clinically acceptable, and have potential uses in the treatment of psychiatric or neurological disorders. Certain aspects and embodiments are described herein and further aspects and embodiments will be evident from the discussion that follows below.

DETAILED DESCRIPTION

Throughout this specification, one or more aspects of the invention may be combined with one or more features described in the specification to define distinct embodiments of the invention.

In the discussion that follows, reference is made to a number of terms, which are to be understood to have the meanings provided below, unless a context expressly indicates to the contrary. The nomenclature used herein for defining compounds, in particular the compounds described herein, is intended to be in accordance with the rules of the International Union of Pure and Applied Chemistry (IUPAC) for chemical compounds, specifically the "IUPAC Compendium of Chemical Terminology (Gold Book)" (see A. D. Jenkins et al., Pure & Appl. Chem., 1996, 68, 2287-2311). For the avoidance of doubt, if a rule of the IUPAC organisation is contrary to a definition provided herein, the definition herein is to prevail.

References herein to a singular of a noun encompass the plural of the noun, and vice-versa, unless the context implies otherwise.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The term "consisting" or variants thereof is to be understood to imply the inclusion of a stated element, integer or step, or group of elements, integers or steps, and the exclusion of any other element, integer or step or group of elements, integers or steps.

The term "about" herein, when qualifying a number or value, is used to refer to values that lie within +5% of the value specified. For example, if a pH range is specified to be about 3.5 to about 6.5, pH values of 3.3 to 6.8 are included.

The formulations of the invention are useful in therapy and may be administered to a patient in need thereof. As used herein, the term 'patient' preferably refers to a mammal. Typically the mammal is a human, but may also refer to a domestic mammal. The term does not encompass laboratory mammals.

The term "treatment" defines the therapeutic treatment of a patient, in order to reduce or halt the rate of progression of a disorder, or to ameliorate or cure the disorder. Prophylaxis of a disorder as a result of treatment is also included. References to prophylaxis are intended herein not to require complete prevention of a disorder: its development may instead be hindered through treatment in accordance with the invention. Typically, treatment is not prophylactic, and the formulation is administered to a patient having a diagnosed or suspected disorder.

As is understood in the art, psychiatric or neurological disorders are disorders which may be associated with one or more cognitive impairment. As used herein, the term 'psychiatric disorder' is a clinically significant behavioural or psychological syndrome or pattern that occurs in an individual and that is associated with present distress (e.g., a painful symptom) or disability (i.e., impairment in one or more important areas of functioning) or with a significantly increased risk of suffering death, pain, disability, or an important loss of freedom.

Diagnostic criteria for psychiatric or neurological disorders referred to herein are provided in the Diagnostic and Statistical Manual of Mental Disorders, Fifth Edition, (DSM-5).

As used herein the term 'obsessive-compulsive disorder' (OCD) is defined by the presence of either obsessions or compulsions, but commonly both. The symptoms can cause significant functional impairment and/or distress. An obsession is defined as an unwanted intrusive thought, image or urge that repeatedly enters the person's mind. Compulsions are repetitive behaviours or mental acts that the person feels driven to perform. Typically, OCD manifests as one or more obsessions, which drive adoption of a compulsion. For example, an obsession with germs may drive a compulsion to clean or an obsession with food may drive a compulsion to overeat, eat too little or throw up after eating (i.e. an obsession with food may manifest itself as an eating disorder). A compulsion can either be overt and observable by others, such as checking that a door is locked, or a covert mental act that cannot be observed, such as repeating a certain phrase in one's mind.

The present invention relates to pharmaceutical formulations suitable for injection, comprising a salt of an optionally substituted dimethyltryptamine compound, a buffer, which is separate to the salt, and water, wherein the formulations have pH values of from about 3.5 to about 6.5 and typical osmolalities of about 250 to about 350 mOsm/Kg.

Human blood serum has a pH of about 7.4 (typically ranging between 7.35 to 7.45, see G. K. Shwalfenberg, *J. Environ. Public Health,* 2012; 2012:727630), and the obvious go-to formulation of salts of optionally substituted dimethyltryptamine compounds is isotonic with a pH of 7.4. It has now been found that formulations described in the prior art or adapted therefrom have non-optimal shelf-life when stored under ambient conditions. The present invention addresses this problem of providing pharmaceutical formulations suitable for injection with substantially reduced degradation products compared with known formulations when stored under stressed conditions. This is indicative of improved shelf-life over such pharmaceutical formulations described in the prior art.

The invention provides a formulation or kit according to the first and second aspect of the invention for use in a method of treating an eating disorder. The term "eating disorder" includes anorexia nervosa, bulimia and binge eating disorder (BED). The symptoms of anorexia nervosa include eating too little and/or exercising too much in order to keep weight as low as possible. The symptoms of bulimia include eating a lot of food in a very short amount of time (i.e. binging) and then being deliberately sick, using laxatives, eating too little and/or exercising too much to prevent weight gain. The symptoms of BED include regularly eating large portions of food until uncomfortably full, and consequently feeling upset or guilty.

As used herein the term 'depressive disorder' includes major depressive disorder, persistent depressive disorder, bipolar disorder, bipolar depression, and depression in terminally ill patients.

As used herein the term 'major depressive disorder' (MDD, also referred to as major depression or clinical depression) is defined as the presence of five or more of the following symptoms over a period of two-weeks or more (also referred to herein as a 'major depressive episode'), most of the day, nearly every day:

depressed mood, such as feeling sad, empty or tearful (in children and teens, depressed mood can appear as constant irritability);

significantly reduced interest or feeling no pleasure in all or most activities;

significant weight loss when not dieting, weight gain, or decrease or increase in appetite (in children, failure to gain weight as expected);

insomnia or increased desire to sleep;

either restlessness or slowed behaviour that can be observed by others;

fatigue or loss of energy;

feelings of worthlessness, or excessive or inappropriate guilt;

trouble making decisions, or trouble thinking or concentrating;

recurrent thoughts of death or suicide, or a suicide attempt.

At least one of the symptoms must be either a depressed mood or a loss of interest or pleasure.

Persistent depressive disorder, also known as dysthymia, is defined as a patient exhibiting the following two features:

A. has depressed mood for most the time almost every day for at least two years. Children and adolescents may have irritable mood, and the time frame is at least one year.

B. While depressed, a person experiences at least two of the following symptoms:
Either overeating or lack of appetite.
Sleeping too much or having difficulty sleeping.
Fatigue, lack of energy.
Poor self-esteem.
Difficulty with concentration or decision-making.

As used herein the term 'treatment resistant major depressive disorder' describes MDD that fails to achieve an adequate response to an adequate treatment with standard of care therapy.

As used herein, 'bipolar disorder', also known as manic-depressive illness, is a disorder that causes unusual shifts in mood, energy, activity levels, and the ability to carry out day-to-day tasks.

There are two defined sub-categories of bipolar disorder; all of them involve clear changes in mood, energy, and activity levels. These moods range from periods of extremely "up," elated, and energised behaviour (known as manic episodes, and defined further below) to very sad, "down," or hopeless periods (known as depressive episodes). Less severe manic periods are known as hypomanic episodes.

Bipolar I Disorder—defined by manic episodes that last at least 7 days, or by manic symptoms that are so severe that the person needs immediate hospital care. Usually, depressive episodes occur as well, typically lasting at least 2 weeks. Episodes of depression with mixed features (having depression and manic symptoms at the same time) are also possible.

Bipolar II Disorder—defined by a pattern of depressive episodes and hypomanic episodes, but not the full-blown manic episodes described above.

As used herein 'bipolar depression' is defined as an individual who is experiencing depressive symptoms with a previous or coexisting episode of manic symptoms, but does not fit the clinical criteria for bipolar disorder.

As used herein, the term 'anxiety disorder' includes generalised anxiety disorder, phobia, panic disorder, social anxiety disorder, and post-traumatic stress disorder.

'Generalised anxiety disorder' (GAD) as used herein means a chronic disorder characterised by long-lasting anxiety that is not focused on any one object or situation. Those suffering from GAD experience non-specific persistent fear and worry, and become overly concerned with everyday matters. GAD is characterised by chronic excessive worry accompanied by three or more of the following symptoms: restlessness, fatigue, concentration problems, irritability, muscle tension, and sleep disturbance.

'Phobia' is defined as a persistent fear of an object or situation the affected person will go to great lengths to avoid, typically disproportional to the actual danger posed. If the feared object or situation cannot be avoided entirely, the affected person will endure it with marked distress and significant interference in social or occupational activities.

A patient suffering a from a 'panic disorder' is defined as one who experiences one or more brief attack (also referred to as a panic attack) of intense terror and apprehension, often marked by trembling, shaking, confusion, dizziness, nausea, and/or difficulty breathing. A panic attack is defined as a fear or discomfort that abruptly arises and peaks in less than ten minutes.

'Social anxiety disorder' is defined as an intense fear and avoidance of negative public scrutiny, public embarrassment, humiliation, or social interaction. Social anxiety often manifests specific physical symptoms, including blushing, sweating, and difficulty speaking.

'Post-traumatic stress disorder' (PTSD) is an anxiety disorder that results from a traumatic experience. Post-traumatic stress can result from an extreme situation, such as combat, natural disaster, rape, hostage situations, child abuse, bullying, or even a serious accident. Common symptoms include hypervigilance, flashbacks, avoidant behaviours, anxiety, anger and depression.

As used herein, the term "post-partum depression" (PPD, also known as postnatal depression) is a form of depression experienced by either parent of a newborn baby. Symptoms typically develop within 4 weeks of delivery of the baby and often include extreme sadness, fatigue, anxiety, loss of interest or pleasure in hobbies and activities, irritability, and changes in sleeping or eating patterns.

As used herein, the term 'substance abuse' means a patterned use of a drug in which the user consumes the substance in amounts or with methods that are harmful to themselves or others.

As used herein, the term 'an avolition disorder' refers to a disorder that includes as a symptom the decrease in motivation to initiate and perform self-directed purposeful activities.

The invention provides a pharmaceutical formulation suitable for injection, comprising a salt of a dimethyltryptamine (DMT) compound optionally substituted with deuterium and optionally substituted at position 4 or 5 with acetoxy or methoxy or position 4 with monohydrogen phosphate; a buffer which is separate to the salt; and water, wherein the formulation has a pH of about 3.5 to about 6.5 and an osmolality of about 250 to about 350 mOsm/Kg.

Owing to the instability of dimethyltryptamine in solution, solutions comprising dimethyltryptamine are generally prepared immediately before or close to the time of use, i.e. storage of solutions of dimethyltryptamine is avoided. Alternatively, solutions of dimethyltryptamine are frozen. The inventors have found that when a buffer, which is separate to the salt, is used, the resultant formulations are more stable than formulations prepared without a buffer separate to the salt. In addition, when a container adapted to prevent penetration of ultraviolet light is used, the resultant formulations are more stable than those stored in containers that allow for ultraviolet light penetration.

The inventors have found that the formulation is surprisingly more stable than formulations prepared at higher pH (specifically those prepared at a pH matching human blood serum, i.e. at a pH of about 7.4). The greater stability of the formulation of the invention relative to the go-to formulation is discussed in more detail in the Example section.

Osmolality is formally defined as the quotient of the negative natural logarithm of the rational activity of water and the molar mass of water, as represented by formula:

$$\text{osmolality} = \frac{-\ln a_w}{18.015}; a_w = \frac{p}{p^*}$$

where p is the partial vapour pressure of water in the solution and p* is the partial vapour pressure of pure water. In simpler terms, osmolality is the number of osmotically active particles (the number of solute particles) in 1 kg of a solution. Thus, osmolality is a function only of the number of particles, and is not related to particle molecular weight, size, shape, or charge (see D. K. Faria et al., M. E. Mendes and N. M. Sumita, *J. Bras. Patol. Med. Lab.*, 53, 1, 38-45 (2017) for a review of the measurement of serum osmolality). For example, one mole of a nondissociating substance (e.g. DMT as a free base) dissolved in 1 kg of water has an osmolality of 1 Osm/kg (1000 mOsm/kg), whilst one mole of a substance that dissociates into two separate species in solution (e.g. DMT fumarate) dissolved in 1 kg of water has an osmolality of 2 Osm/kg (2000 mOsm/kg).

Where a first solution is defined herein to be isotonic with a second solution, the solutions have the same osmolality. For example, where a formulation is defined to be isotonic with human blood serum, the formulation has the same osmolality as human blood serum. Human blood serum typically has an osmolality of about 275 to about 300 mOsm/Kg (L. Hooper et al., *BMJ Open*, 2015; 5 (10): e008846).

The formulation (i.e. of the invention) is suitable for injection, by which is meant that it is in accordance with Pharmacopeial requirements of sterility, contaminants, and pyrogens (see for example The United States Pharmacopeial Convention, General Requirements/(1) Injections, page 33). Sometimes, the formulation contains inhibitors of the growth of microorganisms (e.g. antimicrobial preservatives) and/or anti-oxidants.

Formulations suitable for injection have a pH of about 3 to 9 and an osmolality of about 250 to about 600 mOsm/Kg. pH values above 9 are reported by I. Usach et al. in *Adv. Ther.*, 36, 2986-2996 (2019) to relate to tissue necrosis (death of cells within the tissue), whereas values lower than 3 are reported to cause pain and phlebitis (inflammation of veins). Osmolality values greater than 600 mOsm/Kg are also reported to cause pain. The pH and osmolality of the formulation of the invention lie within the ranges reported to be suitable for injection.

The formulation comprises a salt of a DMT compound optionally substituted with deuterium and optionally substituted at position 4 or 5 with acetoxy or methoxy or position 4 with monohydrogen phosphate, referred to herein as "the DMT compound". Formulations in accordance with this invention may comprise one or more than one DMT compound. For the avoidance of doubt, formulations comprise an optionally substituted DMT salt when they comprise ions of optionally substituted DMT and ions that counter the charge of the optionally substituted DMT ions (counterions). Accordingly, the optionally substituted DMT salt within the formulation may be formed, for example, by contacting optionally substituted DMT as a free base with an aqueous solution comprising an excess of buffer relative to the molar quantity of optionally substituted DMT.

The DMT compound is optionally substituted with deuterium, wherein a deuterium atom is a hydrogen atom with an additional neutron. The DMT compound is also optionally substituted at position 4 or 5 with acetoxy or methoxy or position 4 with monohydrogen phosphate. The term "acetoxy" (often abbreviated to OAc) defines a univalent group derived from acetic acid by removal of a hydrogen atom from the OH moiety. The term "methoxy" (often abbreviated to OMe) defines a univalent group derived from methanol by removal of a hydrogen atom from the OH moiety. The term monhydrogen phosphate defines a divalent group of formula $HPO_4$, derived from phosphoric acid by removal of a proton from two of the three OH moieties, and thus denotes a substituent of formula $—OP(O)(OH)O^-$.

In some embodiments, the dimethyltryptamine compound is optionally substituted at position 5 with methoxy or position 4 with acetoxy or monohydrogen phosphate.

Where the DMT compound is substituted at position 4 with monohydrogen phosphate, this is to reflect that psilocybin (also known as [3-(2-Dimethylaminoethyl)-1H-indol-4-yl] dihydrogen phosphate) in water generally has monohydrogen phosphate at the 4-position, this generally being understood to be the predominant form owing to the pKa values of the two terminal phosphate oxygen atoms being estimated as 1.3 and 6.5. It is further understood that the monohydrogen phosphate-containing form of psilocybin exists as a zwitterion (i.e. an internal salt) in which the nitrogen atom of the dimethylamino moiety is protonated. This form is thus, and psilocybin is to be regarded as, a salt of a DMT compound substituted at position 4 with monohydrogen phosphate.

In some embodiments, the dimethyltryptamine compound is optionally substituted with deuterium at one or more positions selected from the α, β and dimethyl carbon atoms. In further embodiments, the dimethyltryptamine compound is optionally substituted at one or more positions selected from the α and β carbon atoms, such as the α carbon.

For the avoidance of doubt, positions 4, 5, α and β of the optionally substituted DMT salt refer to the positions labelled in the structure below (substitution not shown).

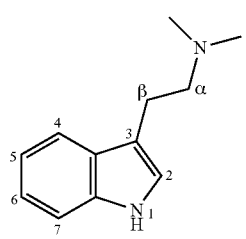

The formulation comprises a buffer, which is separate to the salt, i.e. the buffer is not merely a counterion to the optionally substituted DMT. For example, where the salt is dimethyltryptamine fumarate (i.e. the fumaric acid salt of dimethyltryptamine), an amount of buffer is required over and above the buffer provided by the fumarate. The term "buffer" is well known in the art and refers to a chemical which, on inclusion within a formulation, resists a change in pH on addition of acid or base to the formulation. Within a formulation, a buffer comprises a weak acid and its conjugate base. A suitable buffer comprises an acid with a pKa value that lies within ±1 of the desired pH of the formulation. For example, if the desired pH of the formulation is about 4.0, a suitable buffer comprises a weak acid with a pKa value of from about 3.0 to about 5.0. If the acid of a buffer has more than one pKa value (i.e. each molecule of the acid is able to donate more than one proton), in order for the buffer to be suitable, at least one of the pKa values lies within the desired pH range.

The weak acid and conjugate base of the buffer are in equilibrium with one another. In accordance with Le Chatelier's principle (if a constraint (such as a change in concentration of a reactant) is applied to a system in equilibrium, the equilibrium will shift so as to counteract the effect of the constraint), addition of acid or base to the formulation shifts the position of equilibrium in favour of the conjugate base or weak acid, respectively. Consequently, the concentration of free protons in the formulation (and thus the pH) is relatively unchanged.

As described above, the formulation of the invention has a pH of from about 3.5 to about 6.5. In some embodiments, the buffer comprises an acetate salt and acetic acid (pKa=4.75); a citrate salt and citric acid (pKa=3.13, 4.76 and 6.40); an ascorbate salt and ascorbic acid (pKa=4.17 and 11.6); a benzoate salt and benzoic acid (pKa=4.20); a phosphate salt and phosphoric acid (pKa=2.14, 7.20 and 12.37); an oxalate salt and oxalic acid (pKa=1.25 and 4.14); or a formate salt and formic acid (pKa=3.75). The pKa values cited herein are those reported at 25° C. in water. Typically, the buffer comprises only one of the pairs listed above, i.e. one acid and its conjugate base.

In some embodiments, the buffer comprises an acetate salt and acetic acid; a citrate salt and citric acid; an ascorbate salt and ascorbic acid; a benzoate salt and benzoic acid; or a phosphate salt and phosphoric acid.

In some embodiments, the pH of the formulation is from about 3.75 to about 6.5, such as from about 3.75 to about 5.75. Often, the pH of the formulation is from about 3.75 to about 4.25, typically about 4.0. In such embodiments, the buffer often comprises an acetate salt and acetic acid; a citrate salt and citric acid; an ascorbate salt and ascorbic acid; a benzoate salt and benzoic acid; an oxalate salt and oxalic acid; or a formate salt and formic acid. Sometimes, the buffer comprises an acetate salt and acetic acid; a citrate salt and citric acid; an ascorbate salt and ascorbic acid; or a benzoate salt and benzoic acid.

In some embodiments, the buffer comprises an acetate salt and acetic acid, often sodium acetate and acetic acid, or potassium acetate and acetic acid.

The concentration of buffer within the formulation is typically great enough to resist significant pH change of the formulation on storage of the formulation for two weeks (i.e. the pH typically fluctuates less than about 0.1 pH unit), and is small enough so that the osmolality of the formulation lies within the desired range. The skilled person is able to assess suitable buffer concentrations and to achieve this. Often, the concentration of buffer is from about 15 mM to about 75 mM, such as about 20 mM to about 30 mM. In some embodiments, the concentration of the buffer is about 25 mM.

As described above, the formulation comprises a salt of a DMT compound optionally substituted with deuterium and optionally substituted at position 4 or 5 with acetoxy or methoxy or position 4 with monohydrogen phosphate.

The salt comprises an acid and the DMT compound, or the salt comprises a DMT compound substituted at position 4 with monohydrogen phosphate. An example of a salt comprising an acid and DMT compound is dimethyltryptamine fumarate, which is the fumaric acid salt of dimethyltryptamine. P. H. Stahl and C. G. Wermuth provide an overview of pharmaceutical salts and the acids comprised therein in *Handbook of Pharmaceutical Salts: Properties, Selection and Use*, Weinheim/Zürich: Wiley-VCH/VHCA, 2002. The acids described in this review are suitable acids for inclusion within the salt of the formulation.

The salt may comprise an acid selected from the group consisting of fumaric acid, tartaric acid, citric acid, acetic acid, lactic acid, gluconic acid, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, adipic acid, ascorbic acid, aspartic acid, benzenesulfonic acid, benzoic acid, camphoric acid, camphor-10-sulfonic acid, decanoic acid, hexanoic acid, octanoic acid, carbonic acid, cinnamic acid, cyclamic acid, dodecylsulfuric acid, ethane-1,2-disulfonic acid, ethanesulfonic acid, formic acid, galactaric acid, gentisic acid, glucoheptonic acid, glucuronic acid, glutamic acid, glutaric acid, glycerophosphoric acid, glycolic acid, hippuric acid, hydrobromic acid, hydrochloric acid, isobutyric acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (-L), salicylic acid, sebacic acid, stearic acid, succinic acid, sulfuric acid, thiocyanic acid, toluenesulfonic acid and undecylenic acid.

In some embodiments, where the salt comprises an acid and the DMT compound, the acid is a Brønsted acid having a pKa at 25° C. in water of from about 3 to about 5. In these embodiments, the Brønsted acid may act both as a counterion to the DMT compound and as a buffer. Thus, the formulation may be stabilised to a greater extent, i.e. degradation of the DMT compound may be further ameliorated, when the salt comprises such an acid.

In some embodiments, the salt comprises a Brønsted acid having a pKa at 25° C. of from about 3 to about 5, and a compound of Formula I

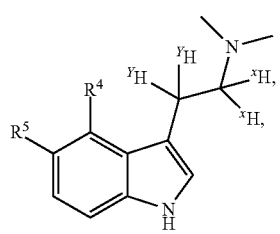

Formula I wherein:
R$^4$ and R$^5$ are both H and each $^X$H and each $^Y$H is independently selected from H and D, or one of R$^4$ and R$^5$ is H and the other is acetoxy or methoxy, each $^Y$H is H and each $^X$H is independently selected from H and D, or the salt comprises a compound of formula I wherein R$^4$ is monohydrogen phosphate, R$^5$ is H and each $^Y$H and each $^X$H is H.

In some embodiments, R$^4$ and R$^5$ are both H. In these embodiments, the DMT compound is any one or a combination of N,N-dimethyltryptamine, α-monodeutero-N,N-dimethyltryptamine, α,α-dideutero-N,N-dimethyltryptamine, α,β-dideutero-N,N-dimethyltryptamine, α,α,β-trideutero-N,N-dimethyltryptamine, α,β,β-trideutero-N,N-dimethyltryptamine and α,α,β,β-tetradeutero-N,N-dimethyltryptamine. Often, the DMT compound is N,N-dimethyltryptamine.

In some embodiments, R$^4$, R$^5$ and each $^Y$H are H and each $^X$H is independently selected from H and D. In these embodiments, the DMT compound is any one or a combination of N,N-dimethyltryptamine, α-monodeutero-N,N-dimethyltryptamine, and α,α-dideutero-N,N-dimethyltryptamine.

Partially deuterated and deuterated N,N-dimethyltryptamine compounds can be synthesised following the reaction schemes (synthetic schemes) provided in Schemes 1 and 2 below. The chemistry depicted in the schemes was reported by PE Morris and C Chiao (*Journal of Labelled Compounds And Radiopharmaceuticals*, Vol. XXXIII, No. 6, 455-465 (1993)). Partially deuterated and deuterated N,N-dimethyltryptamine compounds can also be synthesised following the synthetic scheme depicted in Scheme 3.

Herein, the terms α,α-dideutero-N,N-dimethyltryptamine compounds and α-protio, α-deutero-N,N-dimethyltryptamine compounds are referred to as deuterated (or fully deuterated) N,N-dimethyltryptamine and partially deuterated N,N-dimethyltryptamine respectively. A deuterated (or fully deuterated) N,N-dimethyltryptamine compound thus refers strictly to an N,N-dimethyltryptamine compound with both protons at the α position substituted with deuterium atoms. The term partially deuterated N,N-dimethyltryptamine compound strictly refers to an N,N-dimethyltryptamine compound in which one of the two protons at the α position is substituted with a deuterium atom. A deuterated N,N-dimethyltryptamine compound herein is any N,N-dimethyltryptamine compound substituted with two deuterium atoms at the α position, and a partially deuterated N,N-dimethyltryptamine compound any N,N-dimethyltryptamine compound with one hydrogen atom and one deuterium atom at the α position.

If desired, compositions comprising amounts of N,N-dimethyltryptamine and deuterated N,N-dimethyltryptamine compounds, with the relative proportions of N,N-dimethyltryptamine against deuterated N,N-dimethyltryptamine compounds and partially deuterated N,N-dimethyltryptamine compounds may be controlled by varying the ratio of lithium aluminium hydride and lithium aluminium deuteride in the reducing agent. It is to be understood that in such compositions, R$^4$, R$^5$ and each $^Y$H are H and each $^X$H is independently selected from H and D, i.e. the DMT compound is any one or a combination of N,N-dimethyltryptamine, α-monodeutero-N,N-dimethyltryptamine, and α,α-dideutero-N,N-dimethyltryptamine. Relative proportions may further be varied by adding one or more of N,N-dimethyltryptamine, α,α-dideutero-N,N-dimethyltryptamine and α,α,β,β-tetradeutero-N,N-dimethyltryptamine to the compositions described hereinabove.

Scheme 1: Synthetic pathway for the production of partially deuterated N,N-dimethyltryptamine compounds

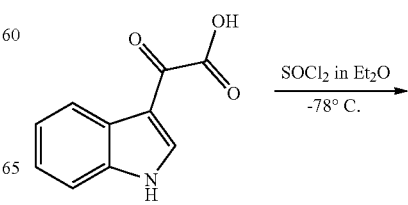

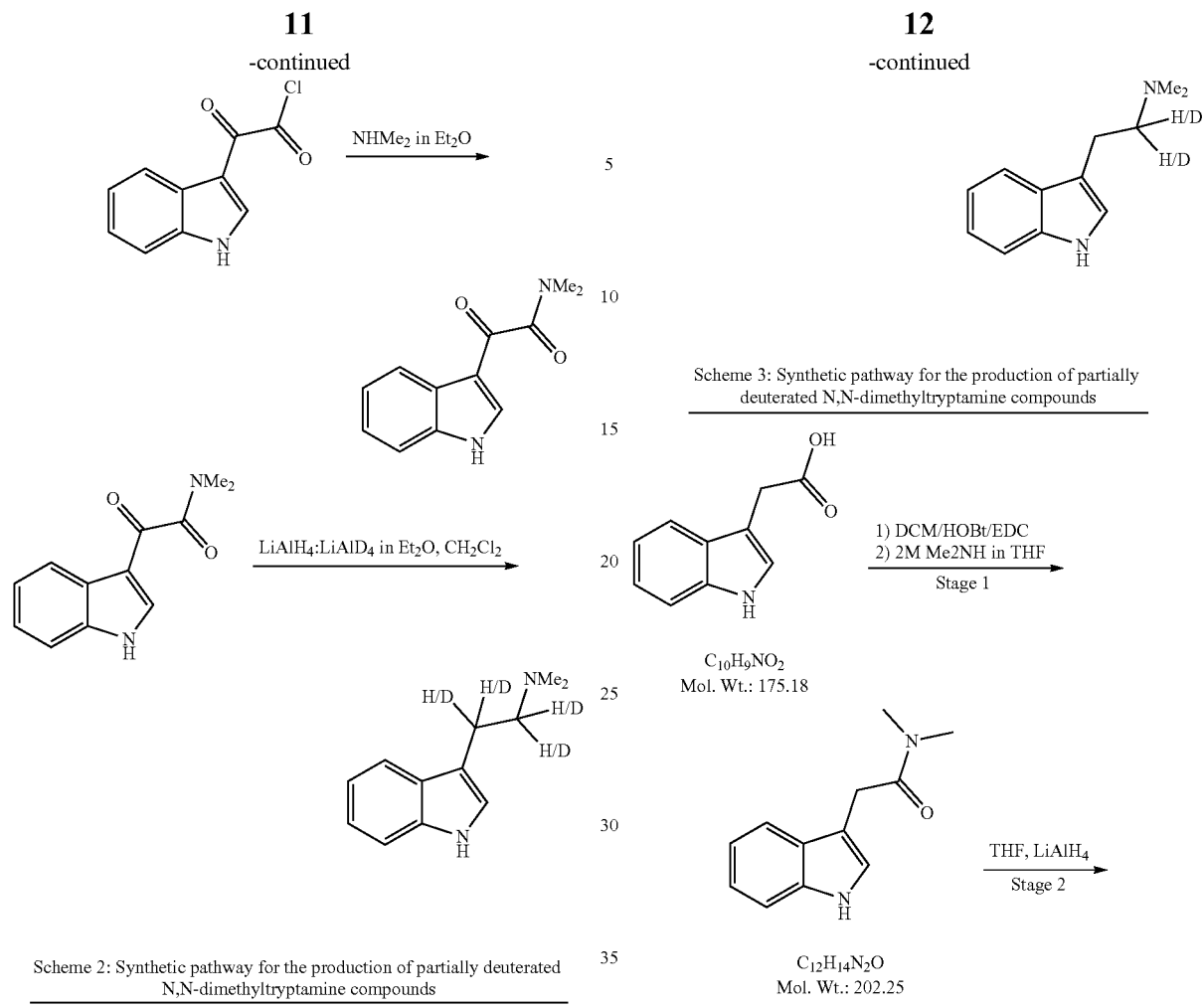

Scheme 2: Synthetic pathway for the production of partially deuterated N,N-dimethyltryptamine compounds

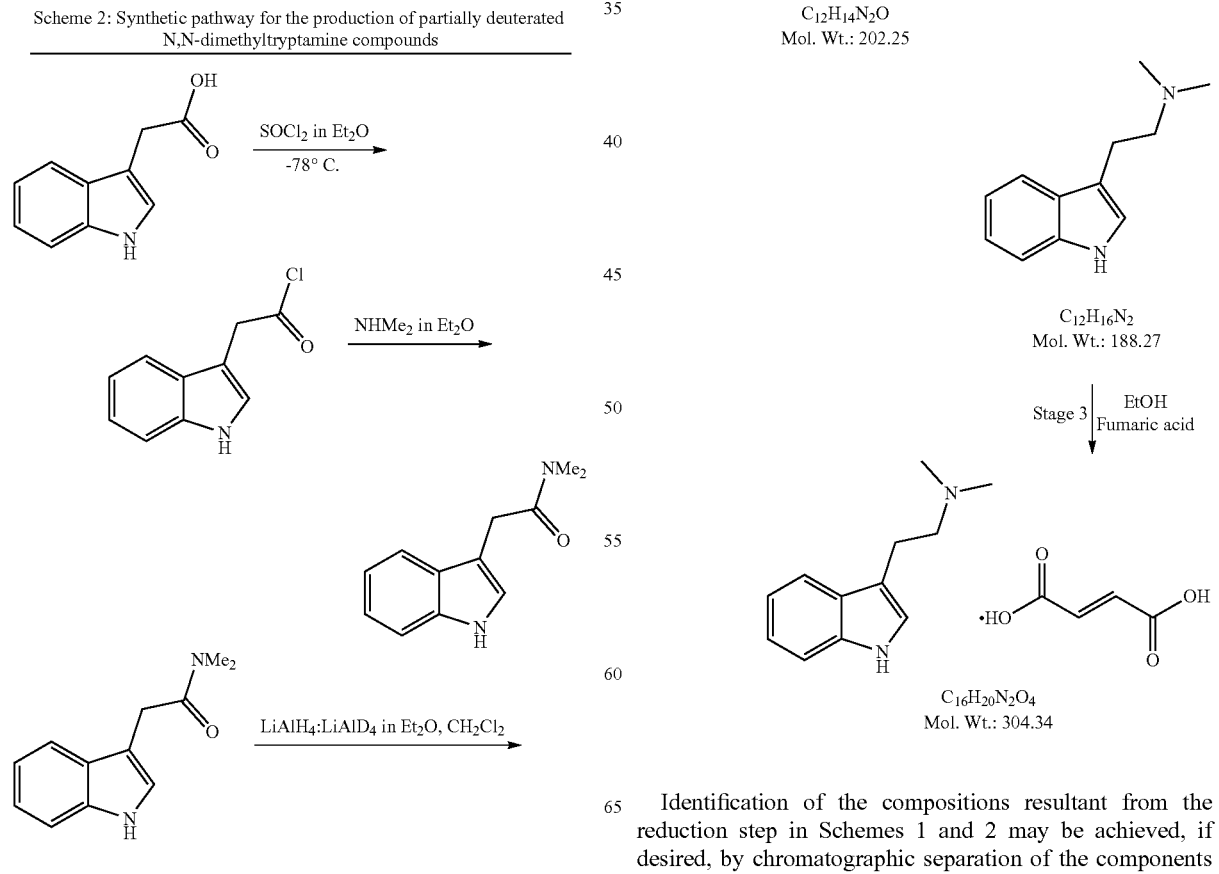

Scheme 3: Synthetic pathway for the production of partially deuterated N,N-dimethyltryptamine compounds Identification of the compositions resultant from the reduction step in Schemes 1 and 2 may be achieved, if desired, by chromatographic separation of the components of the mixtures by conventional means at the disposal of the skilled person in combination with spectroscopic and/or mass spectrometric analysis.

Alternative compositions are obtainable by mixing N,N-dimethyltryptamine, obtainable by Scheme 1 or Scheme 2 when the reducing agent is exclusively lithium aluminium hydride, with a deuterated N,N-dimethyltryptamine compound obtainable from Scheme 1 or Scheme 2 when the reducing agent is exclusively lithium aluminium deuteride.

5-methoxy-α,α-dideutero-N,N-dimethyltryptamine. For example, the DMT compound is 5-methoxy-N,N-dimethyltryptamine.

Scheme 4 represents schemes known in the art to synthesise DMT compounds, in which substituent $R^1$ denotes hydrogen or the substituent $R^4$ or $R^5$, when other than hydrogen, as defined in Formula I; each $R^2$ is methyl and HX refers to the acids described herein with which the DMT compounds described herein may form salts.

Scheme 4: Synthetic pathway for the production of optionally substituted N,N-dimethyltryptamine compounds

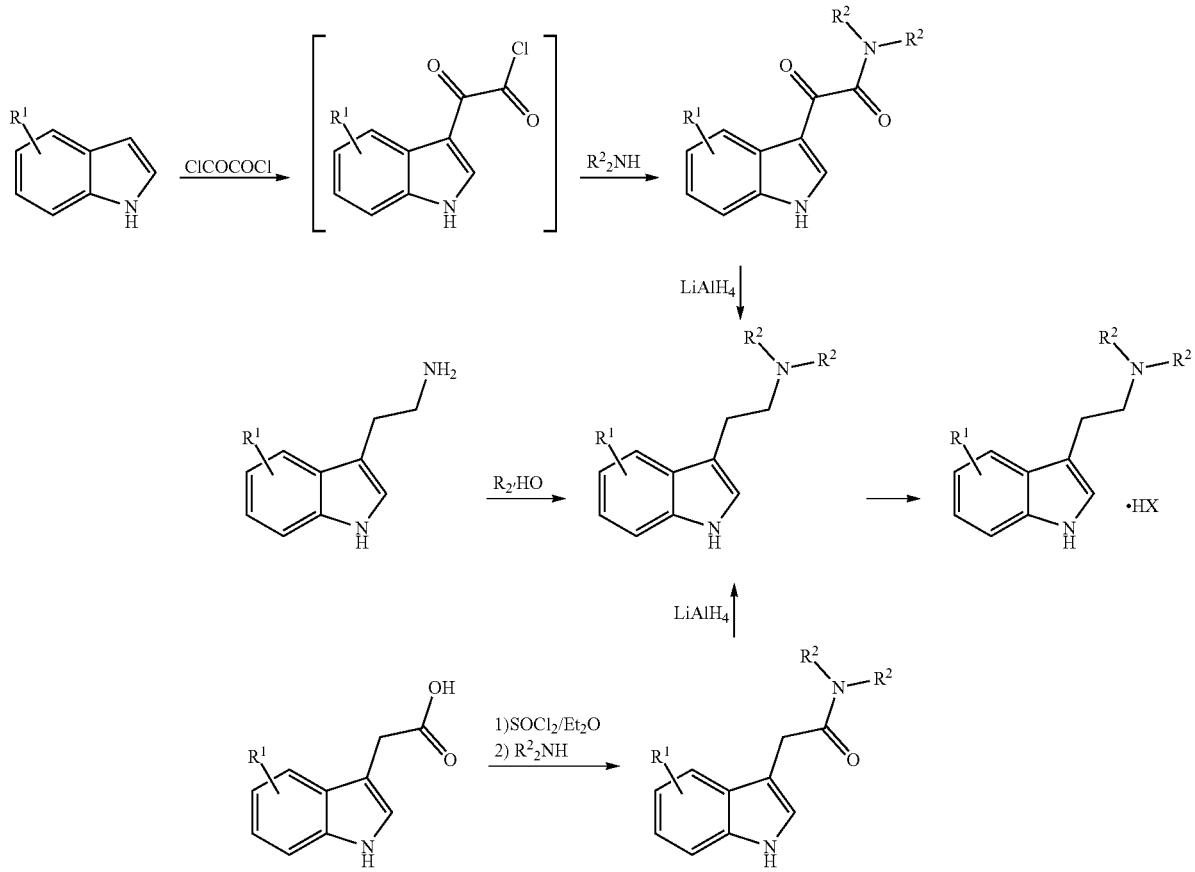

The compositions described hereinabove may be further modified by adding one or more deuterated or partially deuterated N,N-dimethyltryptamine compounds. Stocks of such deuterated or partially deuterated N,N-dimethyltryptamine compounds may be obtained, for example, from the chromatographic separation described above.

In some embodiments, $R^4$ is acetoxy and $R^5$ is H, or $R^5$ is acetoxy and $R^4$ is H. According to some embodiments, $R^4$ is acetoxy and $R^5$ is H, thus the DMT compound is any one or a combination of 4-acetoxy-N,N-dimethyltryptamine, 4-acetoxy-α-monodeutero-N,N-dimethyltryptamine and 4-acetoxy-α,α-dideutero-N,N-dimethyltryptamine. For example, the DMT compound is 4-acetoxy-N,N-dimethyltryptamine.

In some embodiments, $R^4$ is H and $R^5$ is methoxy, or $R^5$ is H and $R^4$ is methoxy. According to some embodiments, $R^4$ is H and $R^5$ is methoxy, thus the DMT compound is any one or a combination of 5-methoxy-N,N-dimethyltryptamine, 5-methoxy-α-monodeutero-N,N-dimethyltryptamine and Mixtures of compounds of Formula I comprising controllable proportions of optionally $R^4$- or $R^5$-substituted DMT and the same optionally $R^4$- or $R^5$-substituted DMT but with α-mono- and/or α,α-di-deuteration may if desired be prepared by reducing 2-(3-indolyl)-N,N-dimethyl acetamide with a desired ratio of lithium aluminium hydride and lithium aluminium deuteride.

For more detail on the synthesis of DMT compounds, see the Example section herein.

In some embodiments, the salt is of an optionally substituted dimethyltryptamine compound and an acid selected from the group consisting of fumaric acid, tartaric acid, citric acid, acetic acid, lactic acid and gluconic acid, typically fumaric acid.

Accordingly, the salt may comprise:
any one or a combination of N,N-dimethyltryptamine, α-monodeutero-N,N-dimethyltryptamine, α,α-dideutero-N,N-dimethyltryptamine, α,β-dideutero-N,N-dimethyltryptamine, α,α,β-trideutero-N,N-dimethyltryptamine, α,β,β-trideutero-N,N-dimethyltryptamine and α,α,β,β-tetradeutero-N,N-dimethyltryptamine; or any one or a combination of 4-acetoxy-N,N-dimethyltryptamine, 4-acetoxy-α-monodeutero-N,N-dimethyltryptamine and 4-acetoxy-α,α-dideutero-N,N-dimethyltryptamine; or any one or a combination of 5-methoxy-N,N-dimethyltryptamine, 5-methoxy-α-monodeutero-N,N-dimethyltryptamine and 5-methoxy-α,α-dideutero-N,N-dimethyltryptamine; and an acid selected from the group consisting of fumaric acid, tartaric acid, citric acid, acetic acid, lactic acid and gluconic acid, typically fumaric acid.

In some embodiments, the salt is DMT fumarate, i.e. it comprises DMT and fumaric acid.

The DMT compound may have a purity of about 80 to 100%. Sometimes, the purity is about 90 to 100%, such as from about 95 to 100%. Typically, the DMT compound has a purity of from about 99 to 100%, i.e. a purity greater than or equal to 99%. Percentages of purity herein are as determined by HPLC.

It is particularly advantageous to prepare the formulations of the present invention with a drug substance comprising the optionally substituted DMT compound or salt thereof with a purity of greater than 99%. By drug substance is meant, as is understood in the art, an active ingredient intended to furnish pharmacological activity or other direct effect in the diagnosis, cure, mitigation, treatment, or prevention of disease or to affect the structure or any function of the patient concerned, but does not include intermediates used in the synthesis of such ingredient. It will be understood that the drug substance may comprise one or more such active ingredients.

Formulations made with less pure drug substance show greater rates of related substances, which is indicative of inferior shelf-life. Accordingly, preferred embodiments of any aspect of the present invention comprise a drug substance comprising an optionally substituted dimethyltryptamine compound or salt thereof having a purity of greater than or equal to 99% when measured by HPLC. Particularly preferred embodiments comprise a drug substance comprising an optionally substituted dimethyltryptamine compound or salt thereof having a purity of greater than or equal to 99.5%, even more preferably 99.7%, and even more preferably 99.9%, when measured by HPLC. The concentration of the DMT compound within the formulation may be any desired concentration, provided that the osmolality of the formulation is about 250 to about 350 mOsm/Kg. The DMT compound may be at a concentration of about 0.001 to about 28 mg/mL, such as about 2.5 mg/ml to about 28 mg/mL. Accordingly, in some embodiments, the formulation of the invention comprises the DMT compound at a concentration of from 2.5 mg/ml to 28 mg/mL, including any integer value within this range. A concentration of 28 mg/mL of DMT provides approximately 148 mOsm/kg (approximately 296 mOsm/kg with counterions taken into account). This allows for the provision of a further 54 mOsm/kg by other components of the formulation, such as the buffer.

In some embodiments, the concentration of the DMT compound within the formulation is about 2.5 mg/mL, which provides approximately 13.2 mOsm/kg (approximately 26.4 mOsm/kg with counterions taken into account).

As described above, the formulation of the invention has an osmolality of about 250 to about 350 mOsm/Kg. As described above, to be injectable, a formulation may have an osmolality of about 250 to about 600 mOsm/Kg. In some embodiments of the invention, the osmolality of the formulation is about 250 to about 500 mOsm/Kg or about 250 to about 400 mOsm/Kg. In some embodiments, the osmolality of the formulation of the invention is about 275 to about 325 mOsm/Kg, such as about 280 to about 310 mOsm/Kg. Typically, the osmolality of the formulation is about 295 to about 305 mOsm/Kg. In some embodiments, the formulation is isotonic with human blood serum.

Sometimes, the concentration of optionally substituted DMT salt and buffer in the formulation gives rise to the desired osmolality. Alternatively, the desired osmolality may be achieved by inclusion of one or more tonicity agents in the formulation. Thus, in some embodiments, the formulation further comprises a tonicity agent. A tonicity agent is defined herein as a chemical that, on inclusion within a formulation, increases the osmolality of the formulation. As described above, the osmolality is the number of osmotically active particles (the number of solute particles) in 1 kg of a solution. Thus, a chemical that acts as a solute when incorporated into the formulation lies within the definition of a tonicity agent.

If the formulation further comprises a tonicity agent, the concentration of tonicity agent depends on the concentration of other components within the formulation, such as the optionally substituted DMT and buffer. For example, where the formulation without tonicity agent has an osmolality of about 60 mOsm/kg, at least about 190 mOsm/kg would be provided by a tonicity agent (e.g. 95 mM of sodium chloride). Inclusion of a tonicity agent is often preferable in low concentration formulations useful for intravenous administration, for example in formulations comprising about 2.5 mg/ml of the DMT compound. In higher concentration formulations, for example those comprising the DMT compound in concentrations greater than about 5 mg/mL, the tonicity agent may be less preferable or absent.

M. F. Powell, T. Nguyen and L. Baloian provide a review of excipients suitable for parenteral administration (administration other than by the mouth or alimentary canal) in *PDA J. Pharm. Sci. Technol.*, 52, 238-311 (1998). All soluble excipients listed in this review article that can be given by the intravenous route will, when added to the formulation, contribute to the osmolality and thus can be considered tonicity agents.

In some embodiments, the tonicity agent is any one or a combination selected from the group consisting of sodium chloride; potassium chloride; dextrose; glucose; mannitol; phosphoric acid; lactose; sorbitol; sucrose; a phosphate salt such as sodium phosphate or potassium phosphate; acetic acid; an acetate salt such as sodium acetate, potassium acetate or ammonium acetate; alanine; ethanol; citric acid; a citrate salt such as sodium citrate or potassium citrate; arginine; ascorbic acid; an ascorbate salt such as potassium ascorbate or sodium ascorbate; benzyl alcohol; calcium chloride; creatinine; edetic acid; an edetate salt such as sodium edetate or calcium edetate; glycine; glycerol; histidine; lactic acid; magnesium chloride; polyethylene glycol; propylene glycol; sodium bicarbonate; sodium hydroxide; hydrochloric acid; lactic acid; lactate salts such as potassium lactate or sodium lactate; tartaric acid and tartrate salts such as sodium tartrate or potassium tartrate.

Some of the tonicity agents listed above may be used to buffer the formulation (e.g. acetate salt, acetic acid, citrate salt, citric acid, ascorbate salt, ascorbic acid, phosphate salt, phosphoric acid). For the avoidance of doubt, where one of the tonicity agents listed above is used as the buffer, it is not also the defined tonicity agent, i.e. where the formulation further comprises a tonicity agent, the tonicity agent is different from the buffer.

Often, the tonicity agent is any one or a combination selected from the group consisting of sodium chloride, potassium chloride, dextrose, glucose, mannitol, lactose, sorbitol and sucrose. Typically, the tonicity agent is sodium chloride.

In some embodiments, the formulation comprises sodium chloride at a concentration of about 120 mM to about 140 mM, such as about 125 mM to about 135 mM. Sometimes, the concentration of sodium chloride within the formulation is about 130 mM.

In some embodiments, the formulation consists essentially of the optionally substituted DMT salt, the buffer, water, and optionally a tonicity agent. By this is meant, for example, that the presence of additional components within the formulation is permitted, provided the amounts of such additional components do not materially affect, in a detrimental manner, the essential characteristics of the formulation. Given that the intention behind including the optionally substituted DMT salt, the buffer, water, and optional tonicity agent in the formulation is to produce a pharmaceutical formulation of optionally substituted DMT suitable for injection, and stable for at least several weeks when stored, it will be understood that the inclusion of components that materially affect, in a detrimental manner, the stability of the formulation or its suitability for injection (e.g. its osmolality or pH), are excluded from the formulation. On the other hand, it will be understood that the presence of any components that do not materially affect, in a detrimental manner, the stability of the formulation or its suitability for injection, is included. Such components include anti-oxidants and antimicrobial preservatives. For an overview of pharmaceutical excipients and their properties, including those with anti-oxidant and antimicrobial properties, see P. J. Sheskey, W G Cook and C G Cable, *Handbook of Pharmaceutical Excipients*, Eighth Edition, Pharmaceutical Press, London 2017.

Anti-oxidants commonly used in aqueous injectable formulations include ascorbic acid, citric acid, tartaric acid, sodium metabisulfite and thiol derivatives.

Antimicrobial preservatives commonly used in injectable formulations include methylparaben (methyl parahydroxybenzoate), ethylparaben (ethyl parahydroxybenzoate) and propylparaben (n-propyl parahydroxybenzoate) benzoic acid, benzyl alcohol, chlorobutanol, phenol and sodium benzoate.

In specific embodiments, the formulation consists of the salt, the buffer, water, and optionally a tonicity agent, i.e. the presence of any other components is excluded.

Often, the formulation has an oxygen content of less than 2 ppm, such as between 0.1 ppm and 2 ppm. The skilled person is able to determine the oxygen content of the formulation using any technique known in the art to be suitable, such as using a dissolved oxygen meter (e.g. a Jenway 970 Enterprise Dissolved Oxygen Meter, available from Keison Products: http://www.keison.co.uk/products/jenway/970.pdf).

The formulation may be stored in any suitable container. In some embodiments, to ameliorate degradation of the formulation further, the formulation is stored in a container adapted to prevent penetration of ultraviolet light, such as amber glass vial. In others, the container within which the formulation is stored is not so adapted (and may be, for example, made of clear glass) with protection against ultraviolet light, if desired, provided by secondary packaging (for example packaging within which the receptacle containing the formulation may be placed). Often, the container is airtight and the formulation is stored under an inert atmosphere, such as under nitrogen or argon, typically nitrogen. The formulation may be stored at room temperature, e.g. at about 20 to about 30° C. or at cooler temperatures, for example at about 2 to about 8° C. Alternatively, to ameliorate degradation of the formulation further, it may be stored in a freezer.

Viewed from a second aspect, the invention provides a kit suitable for preparing a formulation of the first aspect, said kit comprising a salt of a DMT compound optionally substituted with deuterium and optionally substituted at position 4 or 5 with acetoxy or methoxy or position 4 with monohydrogen phosphate; and a buffer, which is separate to the salt.

Also provided is a kit to generate a formulation of the first aspect, the kit comprising:
a first composition comprising a salt of a DMT compound optionally substituted with deuterium and optionally substituted at position 4 or 5 with acetoxy or methoxy or position 4 with monohydrogen phosphate; and
a second composition comprising a buffer, which is separate to the salt,
wherein the first and second compositions are mixed with water and optionally a tonicity agent, and the resulting mixture generates the formulation of the first aspect.

For the avoidance of doubt, embodiments related to the optionally substituted DMT salt and the buffer of the first aspect of the invention as defined herein apply mutatis mutandis to the second aspect. For example, the optionally substituted DMT salt of the kit may comprise a Brønsted acid having a pKa at 25° C. of from about 3 to about 5, and a compound of Formula I and/or the buffer may comprise an acetate salt and acetic acid.

The optionally substituted DMT salt within the kit may be a solid, e.g. in a powder or crystalline form. To ameliorate degradation of the optionally substituted DMT salt in the solid form, the salt may be lyophilised (freeze-dried) before incorporation into the kit. Lyophilising the salt comprises freezing it in the presence of solvent (typically water) and separating the solvent from the salt by sublimation.

The kit may further comprise a tonicity agent. When the kit further comprises a tonicity agent, the embodiments related to the optional tonicity agent of the first aspect of the invention as defined herein apply mutatis mutandis to the second aspect. For example, the tonicity agent may be any one or a combination selected from the group consisting of sodium chloride, potassium chloride, dextrose, glucose, mannitol, lactose, sorbitol and sucrose.

Viewed from a third aspect, the invention provides a method of preparing a pharmaceutical formulation of the first aspect, which is typically a solution. The method comprises contacting the optionally substituted DMT salt, buffer, water and optionally a tonicity agent. For the avoidance of doubt, the embodiments of the first aspect of the invention apply mutatis mutandis to the third aspect. For example, the salt may be DMT, the buffer may comprise acetic acid and an acetate salt, and/or sodium chloride may be used as a tonicity agent.

It will be understood that the contacting of the method may be achieved in a variety of ways. Often, the optionally substituted DMT salt is dissolved in water to form a first solution to which the buffer is added and dissolved, forming a second solution. If a tonicity agent is used, it is often added to and dissolved in the second solution.

In some embodiments, an aqueous solution of the buffer is contacted with the salt, wherein the aqueous solution has a pH of about 3.5 to about 6.5, such as a pH from about 3.75 to about 6.5. Sometimes, the aqueous solution has a pH of about 3.75 to about 5.75, such as a pH from about 3.75 to about 4.25. In some embodiments, the aqueous solution has a pH of about 4.0.

The optionally substituted DMT salt within the formulation may be formed by contacting optionally substituted DMT as a free base with an aqueous solution comprising a quantity of buffer suitable to stabilise the pH and act as counterion to the optionally substituted DMT when protonated. Accordingly, the method of the invention may comprise contacting the optionally substituted dimethyltryptamine in free base form with the buffer, water and optionally a tonicity agent.

In some embodiments, the method further comprises adjusting the pH of the solution resultant from the contacting. Since the pH of the solution resultant from the contacting is usually low, pH adjustment often comprises contacting the solution with a suitable base. The skilled person is able to assess which bases are suitable to adjust the pH of the solution resultant from the contacting without risk of degradation of the optionally substituted DMT salt.

Often, the pH of the solution resultant from the contacting is adjusted with any one selected from the group consisting of sodium hydroxide, potassium hydroxide, sodium carbonate, ammonium hydroxide, calcium hydroxide and magnesium hydroxide. In some embodiments, the pH is adjusted with sodium hydroxide or potassium hydroxide.

As described above, to ameliorate degradation of the formulation further, it may be desirable to minimise the total oxygen content within the container in which the formulation is stored, the oxygen within the container equilibrating between the formulation and the headspace (if any) within the container. Accordingly, it may be desirable to store the formulation under an inert atmosphere for example by purging the headspace to reduce its oxygen content from about 20% typically found in air, to less than, for example, 0.5%. Additionally or alternatively, in some embodiments, the method further comprises sparging the solution resultant from the contacting with an inert gas, such as nitrogen or argon, typically nitrogen.

Viewed from a fourth aspect, there is provided use of a buffer to ameliorate degradation of an injectable pharmaceutical formulation of a salt of a dimethyltryptamine compound optionally substituted with deuterium and optionally substituted at position 4 or 5 with acetoxy or methoxy or position 4 with monohydrogen phosphate.

For the avoidance of doubt, the embodiments of the first aspect of the invention apply mutatis mutandis to the fourth aspect. Specifically, the embodiments of the first aspect relating to the buffer and the optionally substituted DMT salt apply mutatis mutandis to the fourth aspect. For example, the buffer of the fourth aspect may comprise an acetate salt and acetic acid; a phosphate salt and phosphoric acid; a citrate salt and citric acid; an ascorbate salt and ascorbic acid; or a benzoate salt and benzoic acid; and/or the optionally substituted DMT salt of the fourth aspect may comprise a Brønsted acid having a pKa at 25° C. of from about 3 to about 5.

As described above, DMT has a possible therapeutic role in the treatment of depression, obsessive-compulsive disorder, and substance abuse disorders (S. A. Barker, 2018, supra). Viewed from a fifth aspect, therefore, the invention provides a formulation of the first aspect for use in therapy.

Viewed from a sixth aspect, the invention provides a formulation of the first aspect for use in a method of treating a psychiatric or neurological disorder in a patient. Often, the psychiatric or neurological disorder is selected from the group consisting of (i) an obsessive compulsive disorder, (ii) a depressive disorder, (iii) an anxiety disorder, (iv) substance abuse, and (v) an avolition disorder. Often, the disorder is selected from the group consisting of major depressive disorder, treatment resistant major depressive disorder, post-partum depression, an obsessive compulsive disorder and an eating disorder such as a compulsive eating disorder.

Viewed from a seventh aspect, the invention provides a method of treating a psychiatric or neurological disorder comprising administering to a patient in need thereof a formulation of the first aspect. The psychiatric or neurological disorder may be any of those described in relation to the sixth aspect. For example, the disorder may be selected from the group consisting of major depressive disorder, treatment resistant major depressive disorder, post-partum depression, an obsessive compulsive disorder and an eating disorder such as a compulsive eating disorder.

In order to treat the disorder, the formulation comprises an effective amount of the DMT compound, i.e. an amount that is sufficient to reduce or halt the rate of progression of the disorder, or to ameliorate or cure the disorder and thus produce the desired therapeutic or inhibitory effect.

The formulation is suitable for injection, thus its administration in therapy typically comprises injection of the formulation.

The formulation may be suitable for bolus injection, in which a discrete amount of an optionally substituted DMT salt is administered in one injection such that the concentration of DMT in the body quickly increases. Bolus injections are typically administered intravenously (directly into the vein), intramuscularly (within the muscle), intradermally (beneath the skin) or subcutaneously (within the fat or skin).

Each and every reference referred to herein is hereby incorporated by reference in its entirety, as if the entire content of each reference was set forth herein in its entirety.

The invention may be further understood with reference to the following non-non-limiting clauses and examples following thereafter:

A pharmaceutical formulation suitable for injection is described, comprising a salt of a dimethyltryptamine compound optionally substituted with deuterium and optionally substituted at position 4 or 5 with acetoxy or methoxy or position 4 with monohydrogen phosphate; a buffer which is separate to the salt; and water, wherein the formulation has a pH of about 3.5 to about 6.5 and an osmolality of about 250 to about 350 mOsm/Kg. The pH is from about 3.75 to about 6.5, from about 3.75 to about 5.75, from about 3.75 to about 4.25, or about 4.0. The formulation has an osmolality of about 275 to about 325 mOsm/Kg, about 280 to about 310 mOsm/Kg, or about 295 to about 305 mOsm/Kg.

The dimethyltryptamine compound is optionally substituted at position 5 with methoxy or position 4 with acetoxy or monohydrogen phosphate. The dimethyltryptamine compound is optionally substituted with deuterium at one or more positions selected from the α, β and dimethyl carbon atoms. The dimethyltryptamine compound is optionally substituted with deuterium at one or more positions selected from the α and β carbon atoms. The dimethyltryptamine compound is optionally substituted with deuterium once or twice at the α carbon atom.

In some embodiments, the salt comprises a Brønsted acid having a pKa of from about 3 to about 5 and a compound of Formula I

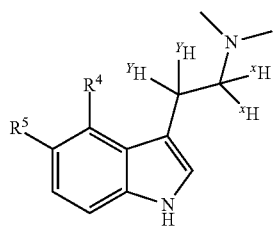

Formula I wherein:

$R^4$ and $R^5$ are both H and each $^XH$ and each $^YH$ is independently selected from H and D, or one of $R^4$ and $R^5$ is H and the other is acetoxy or methoxy, each $^YH$ is H and each $^XH$ is independently selected from H and D, or the salt comprises a compound of formula I wherein $R^4$ is monohydrogen phosphate, $R^5$ is H and each $^YH$ and each $^XH$ is H.

In some embodiments, $R^4$ and $R^5$ are both H. In some embodiments, each $^YH$ is H and each $^XH$ is independently selected from H and D. In some embodiments, $R^4$ is acetoxy and $R^5$ is H. In some embodiments, $R^4$ is H and $R^5$ is methoxy.

In any of the foregoing, the optionally substituted dimethyltryptamine compound may be dimethyltryptamine.

The salt may be of an optionally substituted dimethyltryptamine compound and an acid selected from the group consisting of fumaric acid, tartaric acid, citric acid, acetic acid, lactic acid and gluconic acid. Preferably, the acid is fumaric acid.

The optionally substituted dimethyltryptamine compound may have a purity of greater than 99% by HPLC.

The optionally substituted dimethyltryptamine compound may be at a concentration of about 0.001 to about 28 mg/mL, about 2.5 to about 28 mg/mL, or about 2.5 mg/mL.

In some embodiments, the buffer comprises an acetate salt and acetic acid; a phosphate salt and phosphoric acid; a citrate salt and citric acid; an ascorbate salt and ascorbic acid; a benzoate salt and benzoic acid; an oxalate salt and oxalic acid; or a formate salt and formic acid. In some embodiments, the buffer comprises an acetate salt and acetic acid; a phosphate salt and phosphoric acid; a citrate salt and citric acid; an ascorbate salt and ascorbic acid; or a benzoate salt and benzoic acid. In some embodiments, the buffer comprises an acetate salt and acetic acid. In some embodiments, the buffer comprises sodium acetate and acetic acid, or potassium acetate and acetic acid.

In some embodiments, the formulation comprises the buffer in a concentration of about 15 mM to about 75 mM, about 20 mM to about 30 mM, or about 25 mM.

In some embodiments, the formulation consists essentially of the salt, the buffer, water, and optionally, a tonicity agent. The tonicity agent may be sodium chloride. In some embodiments, the formulation consists of the salt, the buffer, water, and optionally, a tonicity agent.

In some embodiments, the formulation comprises sodium chloride at a concentration of about 120 mM to about 140 mM, about 125 mM to about 135 mM, or about 130 mM.

In some embodiments, the formulation has an oxygen content of less than 2 ppm or between 0.1 ppm and 2 ppm.

In some embodiments, the formulation is stored in a container adapted to prevent penetration of ultraviolet light, for example, in an amber glass vial.

In some embodiments, a kit suitable for preparing a formulation as above is provided, said kit comprising a salt of a dimethyltryptamine compound optionally substituted with deuterium and optionally substituted at position 4 or 5 with acetoxy or methoxy or position 4 with monohydrogen phosphate; and a buffer which is separate to the salt.

In some embodiments, a method of preparing a pharmaceutical formulation as defined as above comprises contacting the salt, buffer, water and optionally a tonicity agent. In some embodiments, an an aqueous solution of the buffer is contacted with the salt, wherein the aqueous solution has a pH as defined in any one of clauses 1 to 5. In some embodiments, the method comprises contacting the optionally substituted dimethyltryptamine in free base form with the buffer, water and optionally a tonicity agent. In some embodiments, the method comprises adjusting the pH of the solution resultant from the contacting. In some embodiments, the pH is adjusted with sodium hydroxide or potassium hydroxide. In some embodiments, the method comprises sparging the solution resultant from the contacting with an inert gas (such as, for example nitrogen).

In some embodiments, a use of a buffer to ameliorate degradation of an injectable pharmaceutical formulation of a salt of a dimethyltryptamine optionally substituted with deuterium and optionally substituted at position 4 or 5 with acetoxy or methoxy or position 4 with monohydrogen phosphate is provided.

In some embodiments, a method of treating a psychiatric or neurological disorder in a patient with the above formulations is provided. The psychiatric or neurological disorder may be selected from the group consisting of (i) an obsessive compulsive disorder, (ii) a depressive disorder, (iii) an anxiety disorder, (iv) substance abuse, and (v) an avolition disorder. The disorder may be major depressive disorder. The disorder may be treatment resistant major depressive disorder. The disorder may be post-partum depression. The disorder may be an obsessive compulsive disorder. The disorder may be an eating disorder (such as, for example, a compulsive eating disorder).

EXAMPLES

Example 1

N,N-DMT 220.9 g (as free base) was prepared as N,N-DMT fumarate, using the chemistry depicted in Scheme 3 above. An additional 4-6 g of six partially deuterated mixtures were also produced using modified conditions.

In Scheme 3, the carbodiimide coupling agent EDC·HCl and additive coupling agent (which enhance the reactivity of the coupling agent) HOBt are used. More generally, the combination of two or more coupling agents comprises an agent selected from (i) a phosphonium coupling agent and a carbodiimide coupling agent selected from DCC, EDC, and DIC; and (ii) an additive coupling agent selected from HOBt, HOOBt, HOSu, HOAt, Ethyl 2-cyano-2-(hydroximino)acetate and DMAP. Often, as exemplified below, EDC is used, preferably as the HCl salt. Often, as exemplified below, the additive coupling agent HOBt. Often, as exemplified below, EDC is used, preferably as the HCl salt in combination with the additive coupling agent HOBt.

Stage 1: Coupling of Indole-3-Acetic Acid and Dimethylamine

To a 5 L vessel under $N_2$ was charged indole-3-acetic acid (257.0 g, 1.467 mol), hydroxybenzotriazole (HOBt, ~20% wet) (297.3 g, 1.760 mol) and dichloromethane (2313 mL) to give a milky white suspension. 1-Ethyl-3-(3-dimethylaminopropyl) carbodiimide hydrochloride (EDC·HCl, 337.5 g, 1.760 mol) was then charged portion-wise over 5 minutes at 16-22° C. The reaction mixture was stirred for 2 hours at ambient temperature before 2M dimethylamine in THF (1100 mL, 2.200 mol) was charged dropwise over 20 minutes at 20-30° C. The resultant solution was stirred at ambient temperature for 1 hour where HPLC indicated 1.1% indole-3-acetic acid and 98.1% target product referred to as Stage 1). The reaction mixture was then charged with 10% $K_2CO_3$ (1285 mL) and stirred for 5 minutes. The layers were separated, and the upper aqueous layer extracted with dichloromethane (643 mL×2). The organic extracts were combined and washed with saturated brine (643 mL). The organic extracts were then dried over $MgSO_4$, filtered and concentrated in vacuo at 45° C. This provided 303.1 g of crude Stage 1 as an off-white sticky solid. The crude material was then subjected to a slurry in tert-butyl methyl ether (TBME, 2570 mL) at 50° C. for 2 hours before being cooled to ambient temperature, filtered and washed with TBME (514 mL×2). The filter-cake was then dried in vacuo at 50° C. to afford Stage 1 266.2 g (yield=90%) as an off-white solid in a purity of 98.5% by HPLC and >95% by NMR.

Stage 2: Preparation of DMT

To a 5 L vessel under $N_2$ was charged Stage 1 (272.5 g, 1.347 mol) and tetrahydrofuran (THF, 1363 mL) to give an off-white suspension. 2.4 M $LiAlH_4$ in THF (505.3 mL, 1.213 mol) was then charged dropwise over 35 minutes at 20-56° C. to give an amber solution. The solution was heated to 60° C. for 2 hours where HPLC indicated Stage 1 ND, target product bracket referred to as Stage 2, 92.5%), Impurity 1 (2.6%), Impurity 2 (1.9%). The complete reaction mixture was cooled to ambient temperature and then charged to a solution of 25% Rochelle's salts (aq) (2725 mL) dropwise over 30 minutes at 20-30° C. The resultant milky white suspension was allowed to stir at 20-25° C. for 1 hour after which the layers were separated and the upper organic layer washed with saturated brine (681 mL). The organic layer was then dried over $MgSO_4$, filtered and concentrated in vacuo at 45° C. The resultant crude oil was subjected to an azeotrope from ethanol (545 mL×2). This provided 234.6 g (yield=92%) of Stage 2 in a purity of 95.0% by HPLC and >95% by NMR.

Stage 3a (i)-(iii): Preparation of Seed Crystals of DMT Fumarate (i) Stage 2 (100 mg) was taken up in 8 volumes of isopropyl acetate and warmed to 50° C. before charging fumaric acid (1 equivalent) as a solution in ethanol. The flask was then allowed to mature at 50° C. for 1 hour before cooling to room temperature and stirring overnight, resulting in a white suspension. The solids were isolated by filtration and dried for 4 hours at 50° C. to provide 161 mg of product (>99% yield). Purity by HPLC was determined to be 99.5% and by NMR to be >95%.

(ii) Substitution of isopropyl acetate for isopropyl alcohol in method (i) afforded a white suspension after stirring overnight. The solids were isolated by filtration and dried for 4 hours at 50° C. to provide 168 mg of product (>99% yield). Purity by HPLC was determined to be 99.8% and by NMR to be >95%.

Substitution of isopropyl acetate for tetrahydrofuran in method (i) afforded a white suspension after stirring overnight. The solids were isolated by filtration and dried for 4 hours at 50° C. to provide 161 mg of product (>99% yield). Purity by HPLC was determined to be 99.4% and by NMR to be >95%.

Analysis by x-ray powder diffraction, showed the products of each of methods 9i) to (iii) to be the same, which was labelled Pattern A.

Stage 3b: Preparation of DMT Fumarate

To a 5 L flange flask under $N_2$ was charged fumaric acid (152.7 g, 1.315 mol) and Stage 2 (248.2 g, 1.315 mol) as a solution in ethanol (2928 mL). The mixture was heated to 75° C. to give a dark brown solution. The solution was polish filtered into a preheated (80° C.) 5 L jacketed vessel. The solution was then cooled to 70° C. and seeded with Pattern A (0.1 wt %), the seed was allowed to mature for 30 minutes before cooling to 0° C. at a rate of 5° C./hour. After stirring for an additional 4 hours at 0° C., the batch was filtered and washed with cold ethanol (496 mL×2) and then dried at 50° C. overnight. This provided 312.4 g (yield=78%) of Stage 3 in a purity of 99.9% by HPLC and >95% by NMR. XRPD: Pattern A.

5-methoxy-DMT fumarate was prepared analogously to the DMT fumarate described immediately above except for the use of 5-methoxyindole-3-acetic acid.

Synthesis of Deuterated Mixtures of DMT Compounds

A modified synthesis at stage 2 using solid $LiAlH_4$/$LiAlD_4$ mixtures was adopted, using 1.8 equivalents of $LiAlH_4$/$LiAlD_4$ versus 0.9 equivalents using the process described above for undeuterated DMT.

Six deuteration reactions were performed.

Representative Synthesis of a Deuterated Mixture (using 1:1 $LiAlH_4$:$LiAlD_4$) of DMT Compounds To a 250 ml 3-neck flask under $N_2$ was charged $LiAlH_4$ (1.013 g, 26.7 mmol), $LiAlD_4$ (1.120 g, 26.7 mmol) and THF (100 mL). The resultant suspension was stirred for 30 minutes before stage 1 (6 g, 29.666 mmol) was charged portion-wise over 15 minutes at 20-40° C. The reaction mixture was then heated to reflux (66° C.) for 2 hours where HPLC indicated no stage 1 remained. The mixture was cooled to 0° C. and quenched with 25% Rochelle's salts (aq) (120 mL) over 30 minutes at <30° C. The resultant milky suspension was stirred for 1 hour and then allowed to separate. The lower aqueous layer was removed and the upper organic layer washed with saturated brine (30 mL). The organics were then dried over $MgSO_4$, filtered and concentrated in vacuo. This provided 4.3 g of crude material. The crude was then taken up in ethanol (52 mL) and charged with fumaric acid (2.66 g, 22.917 mmol) before heating to 75° C. The resultant solution was allowed to cool to ambient temperature overnight before further cooling to 0-5° C. for 1 hour. The solids were isolated by filtration and washed with cold ethanol (6.5 mL×2). The filtercake was dried at 50° C. overnight to provided 5.7 g (yield=63%) of product in a purity of 99.9% by HPLC and >95% by NMR.

Assessment of Extents of Deuteration

This was achieved by LCMS-SIM (SIM=single ion monitoring), the analysis giving a separate ion count for each mass for the three deuterated N,N-dimethyltryptamine compounds (N,N-dimethyltryptamine (DO), α-deutero-N,N-dimethyltryptamine (D1) and α,α-dideutero-N,N-dimethyltryptamine (D2) at the retention time for N,N-dimethyltryptamine. The percentage of each component was then calculated from these ion counts.

For example, % D0=[D0/(D0+D1+D2)]×100.

| HPLC Parameters | |
|---|---|
| System: | Agilent 1100/1200 series liquid chromatograph or equivalent |
| Column: | Triart Phenyl; 150 × 4.6 mm, 3.0 μm particle size (Ex: YMC, Part number: TPH12S03-1546PTH) |
| Mobile phase A: | Water: Trifluoroacetic acid (100:0.05%) |
| Mobile phase B: | Acetonitrile: Trifluoroacetic acid (100:0.05%) |

| Gradient: | Time | % A | %B |
|---|---|---|---|
| | 0 | 95 | 5 |
| | 13 | 62 | 38 |
| | 26 | 5 | 95 |
| | 30.5 | 5 | 95 |
| | 31 | 95 | 5 |

| | | | |
|---|---|---|---|
| Flow rate: | 1.0 mL/min | | |
| Stop time: | 31 minutes | Post runtime: | 4 minutes |
| Injection volume: | 5 μL | Wash vial: | N/A |
| Column temperature: | 30° C. combined | | |
| Wavelength: | 200 nm, (4 nm) Reference: | | N/A |

Mass spectrometry parameters

| | | | |
|---|---|---|---|
| System: | Agilent 6100 series Quadrupole LC-MS or equivalent | | |
| Drying gas flow: | 12.0 L/min | Drying gas temp.: | 350° C. |
| Nebuliser pressure: | 35 psig | | |
| Fragmentor: | 110 | Gain: | 1.00 |

| Cpd | RT | RRT | Conc | Diluent | Detection | Mass |
|---|---|---|---|---|---|---|
| D0 | 10.64 | 1.00 | 0.30 mg/ml | $CH_3CN:H_2O$ (50:50) | (+) SIM 189.10 | m/z |
| D1 | 10.64 | 1.00 | 0.30 mg/ml | $CH_3CN:H_2O$ (50:50) | (+) SIM 190.10 | m/z |
| D2 | 10.64 | 1.00 | 0.30 mg/ml | $CH_3CN:H_2O$ (50:50) | (+) SIM 191.10 | m/z |

MS-SIM range is the target mass ± 0.1 m/z

The data for the six deuterated reactions are tabulated in Table A below:

TABLE A

| Mixture No. ($LiAlH_4:LiAlD_4$ ratio) | Input (stage 1) | Output stage 3 (yield) | Purity by HPLC | Purity by NMR | Deuteration % $D_0$ | $D_1$ | $D_2$ |
|---|---|---|---|---|---|---|---|
| 1 (SPL028) (0:1) | 5 g | 5.3 g (65%) | 99.7% | >95% | 0.7% | 2.7% | 96.6% |
| 2 (1:1) | 6 g | 5.699 g (63%) | 99.9% | >95% | 30.0% | 48.3% | 21.7% |
| 3 (1:2) | 5 g | 4.206 g (52%) | 99.9% | >95% | 16.5% | 46.8% | 36.8% |
| 4 (1:3) | 5 g | 5.558 g (68%) | 99.8% | >95% | 9.3% | 41.5% | 49.2% |
| 5 (2:1) | 5 g | 4.218 g (52%) | 99.9% | >95% | 47.5% | 41.3% | 11.2% |
| 6 (3:1) | 5 g | 5.0 g (62%) | 99.4% | >95% | 57.5% | 35.3% | 7.4% |

To synthesise 5-methoxy-N,N-dimethyltryptamine or 4-methoxy-N,N-dimethyltryptamine, 3-indoleacetic acid (see Scheme 3) may be replaced with 5-methoxyindole-3-acetic acid (see synthesis of α,α-dideutero-5-methoxydimethyltryptamine described below) or 4-methoxyindole-3-acetic acid respectively, both of which are commercially available (for 5-methoxyindole-3-acetic acid, for example from Sigma-Aldrich (code M14935-1G), for 4-methoxyindole-3-acetic acid see for example Aaron chemicals (code AR00VTP1).

5-methoxy-N,N-dimethyltryptamine (see Sigma-Aldrich code M-168-1ML), 4-methoxy-N,N-dimethyltryptamine (see Cayman Chemical code 9000895), 4-acetoxy-N,N-dimethyltryptamine (see Cayman Chemical code 14056) and 3-[2-(Dimethylamino)ethyl]-1H-indol-4-yl phosphate (psilocybin, see Sigma-Aldrich CAS Number 520-52-5) are also commercially available.

Synthesis of α,α-dideutero-5-methoxydimethyltryptamine

Stage 1:

To a 100 mL 3-neck flask under $N_2$ was charged 5-methoxyindole-3-acetic acid (3.978 g, 19.385 mmol), HOBt (~20% wet) (3.927 g, 23.261 mmol) and DCM (40 mL). EDC·HCl (4.459 g, 23.261 mmol) was then charged in portions over 15 minutes at <30° C. The reaction mixture was stirred at ambient temperature for 1 hour before being charged with 2 M dimethylamine (14.54 mL, 29.078 mmol) dropwise over 15 minutes at <25° C. After stirring for 1 hour HPLC indicated no SM remained. The reaction mixture was then charged with 10% $K_2CO_3$ (20 mL), stirred for 5 minutes then allowed to separate. The lower aqueous layer was removed and back extracted with DCM (10 mL×2). The organic extracts were combined, washed with saturated brine (10 mL) then dried over $MgSO_4$ and filtered. The filtrate was concentrated in vacuo at 45° C. to provide 3.898 g active (yield=87%) of product in a purity of 95.7% by HPLC.

Stage 2

To a 100 mL 3-neck flask under $N_2$ was charged Stage 1 methoxy derivative (3.85 g, 16.586 mmol) and THF (19.25 mL). 2.4 M $LiAlD_4$ in THF (6.22 mL, 14.927 mmol) was then charged dropwise over 30 minutes at <40° C. The reaction mixture was heated to 60° C. for 1 hour where HPLC indicated 0.1% SM remained. The reaction mixture was then cooled to ambient temperature and quenched into 25% Rochelle's salts (38.5 mL) dropwise over 30 minutes at <30° C. The resultant suspension was stirred for 1 hour before being allowed to separate. The lower aqueous layer was then removed, and the upper organic layer washed with saturated brine (9.6 mL). The organics were then dried over $MgSO_4$, filtered and concentrated in vacuo before being subjected to an azeotrope from EtOH (10 ml×2). This provided 3.196 g active (yield=88%) of product in a purity of 91.5% by HPLC.

Stage 3

To a 50 mL 3-neck flask under $N_2$ was charged fumaric acid (1.675 g, 14.430 mmol) and a solution of Stage 2 methoxy derivative (3.15 g, 14.299 mmol) in EtOH (37.8 mL). The mixture was then heated to 75° C. for 1 hour, this did not produce a solution as expected, the mixture was further heated to reflux (78° C.) which still failed to provide a solution. The suspension was therefore cooled to 0-5° C., filtered and washed with EtOH (8 mL×2) before being dried at 50° C. overnight. This provided 3.165 g (yield=65%) of material in a purity of 99.9% by HPLC.

Development of Formulation

A stable formulation isotonic with human blood serum and suitable for intravenous (IV) bolus administration of DMT fumarate was developed. A suitable process for preparation of such a formulation comprising DMT fumarate at a concentration of 2.5 mg/mL was also developed. These formulations were prepared and placed under accelerated storage to assess stability over several weeks.

All stated concentrations below are expressed in terms of the free base (i.e. in the absence of fumarate counterion). To do so, a correction factor of 1.59 has been applied to the specific batch of drug substance as supplied.

Experimental Details

Initial Tests

Solubility of DMT fumarate was assessed at a concentration of 10 mg/mL in a small selection of aqueous vehicles (water, saline, 20 mM phosphate buffer and a combination of buffer and saline).

Phosphate buffer (100 mL) was prepared using 219.53 mg of the dibasic form $[HPO_4][Na]_2$ with 183.7 mg of the monobasic form $[H_2PO_4]Na$, both dihydrate salts. The solution was adjusted to pH 7.0 with addition of NaOH (1 M) and then made to volume. 10 ml of a 10 mg/mL formulation was prepared.

A phosphate buffer combined with saline was initially tested (20 mM phosphate buffer in 0.45% w/v saline) as a good starting point for a physiologically acceptable formulation with no solubility issues. To prepare this, sodium chloride was first dissolved in water to produce the saline solution (100 mL, 0.45% w/v). The phosphate salts, in the quantities described above, were then dissolved in the saline solution and the pH was adjusted using NaOH (1 M).

DMT fumarate was readily soluble in each aqueous vehicle. In terms of appearance, each solution was a clear beige colour, which on filtration (using 0.2 μm filters) was removed to produce a clear colourless solution. The pH of these solutions was in the range 3-4.

Buffer strength at 30 and 50 mM (as phosphate buffer, pH 7.4, prepared in 0.45% w/v sodium chloride) was tested to assess the effect of the buffer on pH control of formulations comprising concentrations of 2 or 2.5 mg/mL DMT fumarate. This buffer strength range was chosen in order to determine the required buffer strength so as to fix the pH of the formulation to about pH 7.4. When developing formulations for injection, it is typical to match the pH of the formulation with those of the patient's blood serum. Human blood serum has a pH of about 7.4. The buffers were prepared as follows. Saline solution was prepared by dissolving 9 g of sodium chloride in 2 litres of water. The phosphate salts (e.g. 30 mM=dibasic dihydrate (4.29 g), monobasic dihydrate (1.43 g), 50 mM=dibasic dihydrate (7.28 g), monobasic dihydrate (2.25 g) were dissolved into the saline solution the pH was adjusted to 7.4 using NaOH (1 M). 9 g of NaCl in 2 litres of water. pH adjustment to pH 7.4 with 1M NaOH.

The initial pH of each solution following preparation was less than pH 7.4. At 20 mM the initial pH value of 5.9 continued to drop on storage of the solution overnight in the laboratory, indicating that the buffering capacity of the buffer at 20 mM concentration was insufficient. At both 30 mM and 50 mM buffer strengths, the initial pH values were >6.5 and remained stable.

A short-term stability assessment was performed and data obtained for the pH, osmolality and assay are presented in Tables 1 and 2. The data in Table 2 were obtained on storage of the formulations at between 40 to 50° C.

TABLE 1

Short-term formulation stability assessment

| Sample | pH | | | | Osmolality (mOsm/kg) | | | | Assay (mg/ML) | | | |
|---|---|---|---|---|---|---|---|---|---|---|---|---|
| | Initial | 24 hr | Day 5 | Day 7 | Initial | 24 hr | Day 5 | Day 7 | Initial | 24 hr | Day 5 | Day 7 |
| 2 mg · mL$^{-1}$/30 mM buffer/light$^a$ | 6.74 | 6.74 | — | 6.71 | 239 | 238 | — | 244 | 2.00 | 2.02 | — | 2.09 |
| 2 mg · mL$^{-1}$/30 mM buffer/dark$^b$ | 6.74 | 6.73 | — | 6.72 | 239 | 235 | — | 253 | — | 1.99 | — | 2.05 |
| 2 mg · mL$^{-1}$/30 mM buffer/2-8° C. | 6.74 | 6.73 | — | 6.72 | 239 | 238 | — | 237 | 1.99 | 1.96 | — | 2.09 |
| 2 mg · mL$^{-1}$/50 mM buffer/light$^a$ | 6.95 | 6.96 | — | 6.95 | 285 | 284 | — | 289 | 1.95 | 1.99 | — | 2.04 |
| 2 mg · mL$^{-1}$/50 mM buffer/dark$^b$ | 6.85 | 6.98 | — | 6.95 | 285 | 285 | — | 286 | — | — | — | 2.04 |
| 2 mg · mL$^{-1}$/50 mM buffer/2-8° C. | 6.95 | 6.97 | — | 6.95 | 285 | 284 | — | 283 | 1.98 | 1.98 | — | 2.08 |
| 2.5 mg · mL$^{-1}$/50 mM buffer/light$^a$ | 6.87 | — | 6.86 | — | 288 | — | 286 | — | 2.46 | — | 2.51 | — |
| 2.5 mg · mL$^{-1}$/50 mM buffer/dark$^b$ | 6.87 | — | 6.86 | — | 288 | — | 287 | — | 2.43 | — | 2.60 | — |
| 2.5 mg · mL$^{-1}$/50 mM buffer/2-8° C. | 6.87 | — | 6.86 | — | 288 | — | 288 | — | — | — | 2.57 | — |

$^{a,b}$Light and dark at laboratory temperature storage (15-25° C.)

TABLE 2

Short-term formulation stability assessment

| Sample | pH Initial | pH Day 7 | Assay (mg/mL) Initial | Assay (mg/mL) Day 7 | Related Substances (%) Initial | Related Substances (%) Day 7 |
|---|---|---|---|---|---|---|
| 2.5 mg/mL/50 mM buffer | 6.88 | 6.87 | 2.49 | 2.38 | N.D <0.02 | 1.13 |
| 2.5 mg/mL/50 mM buffer ($N_2$ sparged) | 6.88 | 6.87 | 2.49 | 2.55 | N.D <0.02 | ND <0.02 |
| 2.5 mg/mL/50 mM buffer (2-8° C.) | 6.88 | 6.89 | 2.49 | 2.53 | N.D <0.02 | ND <0.02 |
| 2.5 mg/mL/50 mM buffer (UV light exposure) | 6.83 | — | 2.10 | — | 3.57 | — |
| 2.5 mg/mL/50 mM buffer (UV light exposure Control) | 6.84 | — | 2.50 | — | N.D <0.02 | — |

Noticeably, the go-to buffers stored under ambient conditions (1 week at 40° C.), without $N_2$ sparging or control of UV light exposure, contained 1.13% of related substances after 1 week of storage. This is compared to the related substances formed under the same conditions for Britton-Robinson buffered formulations below.

Development of Formulation

Materials

Details of the DMT fumarate employed for stability purposes are provided in Table 3 and excipients used are listed in Table 4.

TABLE 3

DMT fumarate used for the stability study

| Material | Batch Number | Supplier |
|---|---|---|
| DMT fumarate | SPL026 | Onyx Scientific, Sunderland |

TABLE 4

Excipients used for the formulation development study

| Material | Batch Number | Supplier |
|---|---|---|
| Purified water | Not applicable | Elga dispenser, asset number ARC37642 |
| Sodium chloride | 17D194102 | VWR |
| di-Sodium hydrogen orthophosphate dihydrate | 1997160 | Fisher Chemicals |
| Sodium dihydrogen orthophosphate dihydrate | 1724808 | Fisher Chemicals |
| Volumetric 1M sodium hydroxide solution | 726144 | Scientific Laboratory Supplies |
| Glacial acetic acid | 1727841 | Fisher Chemicals |

Equipment

Equipment, excluding standard laboratory glassware, used throughout the studies is listed in Table 5. Calibration and verification of equipment were performed in accordance with standard operating procedures for all measurements, as required.

TABLE 5

Typical equipment used during the formulation development study

| Item | Make and Model | Asset Number |
|---|---|---|
| Balance | Mettler Toledo, MX5 | 32721 |
| Balance | Sartorius, ME215S | 31476 |
| Single Stir Plate | Bibby HB502 | 20234 |
| pH Meter | Mettler Toledo, MP225 | 20322 |
| Osmolality | Advanced Instruments Osmo 1 | 38564 |
| Filters | Millex MP PES 0.22 µm | n/a |
| Light Box | Heraeus SunTest | 28 694 |

Osmolality Readings

Osmolality readings were obtained using an Advanced Instruments Osmo1 instrument. A single sample syringe was used to introduce the sample into the osmometer, which employed the industry-preferred principles of freezing point depression to determine osmolality accurately and precisely.

Instrument verification was performed using 50, 850 and 2000 mOsm/kg $H_2O$ calibration standards prior to analysis, for confirmation of accuracy.

pH Readings pH readings were obtained using a Mettler Toledo MP225 PH meter. The electrode probe was inserted into the test solutions, contained in a glass vial, with brief stirring at ambient temperature.

Instrument verification was performed prior and post each use using, as supplied, pH buffer solutions over the range pH 1.68 to 10.01 for confirmation of accuracy.

High Performance Liquid Chromatography (HPLC)

The following HPLC parameters were employed to assess assays and the quantity of related substances (substances resulting from DMT fumarate degradation) of solutions of DMT fumarate that were prepared as part of the formulation development.

| | |
|---|---|
| Column: | YMC-Triart Phenyl; 150 × 4.6 mm, 3 µm, |
| Mobile phase A: | Water:Trifluoroacetic acid (100:0.05 v/v) |
| Mobile phase B: | Acetonitrile:Trifluoroacetic acid (100:0.05 v/v) |
| Diluent: | Acetonitrile: Water (50:50) |

| Gradient timetable: | Time (min) | % A | % B |
|---|---|---|---|
| | 0.0 | 95 | 5 |
| | 13.0 | 62 | 38 |
| | 26.0 | 5 | 95 |
| | 30.5 | 5 | 95 |
| | 31.0 | 95 | 5 |

| | |
|---|---|
| Flow rate: | 1.0 mL · min$^{-1}$ |
| Column temperature: | 30° C. |
| Injection volume: | 7.5 µL |
| Needle wash: | Water: Acetonitrile (50:50) |
| Seal Wash: | Water: Acetonitrile (50:50) |
| Run time: | 35 minutes |
| Detection Wavelength: | 220 nm |

Formulation Development

The solubility of DMT fumarate was initially assessed over a range of different pH values, from pH 4 to pH 10. Formulations were then prepared at the target concentration of 2.5 mg/ml of DMT fumarate over a pH range of pH 4 to pH 9.

Solubility of DMT Fumarate at Different pH Values

Seven solutions, each containing a concentration of 20 mg/ml of DMT fumarate were prepared in Britton-Robinson (B-R) buffer solution. On dissolution of DMT fumarate in each test formulation (DMT fumarate was very soluble, needing only swirling and shaking in each), the pH of each test formulation was then adjusted to pH 4, 5, 6, 7, 8 and 9 using sodium hydroxide solution.

Solubility of a concentration of 20 mg/ml of DMT fumarate was confirmed at pH 4, 5, 6 and 7—these solutions were clear and colourless. The sample at pH 8 was hazy and the samples at pH 9 and pH 10 contained a precipitate. Following overnight storage under ambient conditions, the pH of each solution was measured and the results showed no changes from the initial pH values. Each sample was then filtered and analysed for content. Each solution, including the high pH solutions where precipitate was present, contained approximately the same content of DMT fumarate.

pH Stability pH-stability of DMT fumarate at a concentration of 2.5 mg/ml was assessed in 40 mM Britton-Robinson buffer solution over the buffer solution range pH 4 to 9 (nominal). The pH of each formulation was measured at preparation, following 7 days storage at 40° C. and then further storage over an additional 3 days at 40° C. and 7 days at 50° C. (so a total further storage of 10 days). Analysis of these formulations was performed on preparation, and then after 7 and 17 days storage for content (assay) and related substances.

Two extra aliquots of the pH 7 (nominal) solution were taken for additional testing, one was sparged with nitrogen and the second was stressed under intense UV light for 4 hours equivalent to 1 ICH unit (200 watt hours UVA, 0.6 million luxhours).

On preparation of each formulation, there was a drop in pH in the range of 0.14 units (pH 4 formulation) to 1.29 units (pH 9 formulation) this being due to the acidic nature of the drug substance. Once prepared, the pH of each formulation remained stable at the two subsequent stability time points (Table 6).

The concentration of DMT fumarate was determined by HPLC at preparation and on the two subsequent stability occasions (Table 7). All results confirmed accurate preparation with no significant concentration changes on either Day 7 or Day 17. The only significant change over the course of the experiment was a drop in concentration following light stressing of the aliquot of the nominal pH 7 formulation. This was accompanied by a significant increase in observed degradants.

In terms of related substances, only peaks greater than 0.05% of the total peak area have been reported. The summarised related substances data are presented in Table 8, with individual values in Table 9 (7 days storage at 40° C.) and Table 10 (10 days storage at 40° C. with a further 7 days storage at 50° C.).

At preparation, no related substances peaks were present. On Day 7 only the pH 9 formulation contained a peak at a relative retention time of 1.11. With only minimal additional peaks observed following the 7 days elevated storage, the formulations were further stressed (with an increase in storage temperature over time) and on analysis after 17 days storage, additional peaks were present in several of the formulations with a clear trend visible with increasing numbers of peaks and peak area with increasing pH, ranging from no peaks (pH 4) to 3 peaks with a total peak area of 0.61% (pH 9). The nitrogen sparged formulation (pH 7) was significantly more robust than its unsparged equivalent confirming that oxidation is a degradation pathway. The light stressed formulation was the most degraded sample with a total related substances value of 1.68%.

TABLE 6 pH-stability measurement for SPL026 in Britton-Robinson buffer

| Nominal pH | Initial | Day 7[b] | Day 17[c] |
|---|---|---|---|
| 4.0 | 3.86 | 3.84 | 3.84 |
| 5.0 | 4.57 | 4.55 | 4.52 |
| 6.0 | 5.08 | 5.07 | 5.06 |
| 6.5 | 5.33 | 5.33 | 5.31 |
| 7.0 | 6.12 | 6.10 | 6.10 |
| 6.5 sparged $N_2$ | 6.12 | 6.18 | 6.09 |
| 7.0 UV Light | 6.07[a] | — | — |
| 7.5 | 6.60 | 6.58 | 6.59 |
| 8.0 | 6.87 | 6.86 | 6.84 |
| 9.0 | 7.71 | 7.72 | 7.70 |

[a] pH on completion of testing
[b] 7 days storage at 40° C.
[c] 10 days storage at 40° C. followed by 7 days at 50° C.

TABLE 7 pH-stability for SPL026 in Britton-Robinson buffer (assay)

| | Concentration (mg·mL$^{-1}$) | | | |
|---|---|---|---|---|
| Nominal pH | Initial | Day 7[b] | Day 17[c] | Light |
| 4.0 | 2.47 | 2.57 | 2.52 | — |
| 5.0 | 2.50 | 2.48 | 2.52 | — |
| 6.0 | 2.51 | 2.56 | 2.48 | — |
| 6.5 | 2.49 | 2.59 | 2.51 | — |
| 7.0 | 2.54 | 2.54 | 2.45 | — |
| 7.0 sparged $N_2$ | 2.54 | 2.54 | 2.51 | — |
| 7.0 UV Light | 2.54 | — | — | 2.26[a] |
| 7.5 | 2.50 | 2.55 | 2.46 | — |
| 8.0 | 2.49 | 2.49 | 2.42 | — |
| 9.0 | 2.47 | 2.41 | 2.46 | — |

[a] concentration on completion of light stressing (200 watt hours UVA, 0.6 million luxhours). This sample was an aliquot of the pH 7 solution
[b] 7 days storage at 40° C.
[c] 10 days storage at 40° C. followed by 7 days at 50° C.

TABLE 8 pH stability total related substances assay for SPL026 in Britton-Robinson buffer

| | Total related substances (%) | | | |
|---|---|---|---|---|
| Nominal pH | Initial | Day 7[b] | Day 17[c] | Light |
| 4.0 | ND | ND | ND | — |
| 5.0 | ND | ND | 0.07 | — |
| 6.0 | ND | ND | 0.09 | — |
| 6.5 | ND | ND | 0.10 | — |
| 7.0 | ND | ND | 0.26 | — |
| 7.0 sparged $N_2$ | ND | ND | 0.05 | — |
| 7.0 UV Light | ND | — | — | 1.68[a] |
| 7.5 | ND | ND | 0.42 | — |
| 8.0 | ND | ND | 0.58 | — |
| 9.0 | ND | 0.10 | 0.61 | — |

ND - <0.02 area of total peak area
[a] % related substances on completion of light stressing (200 watt hours UVA, 0.6 million luxhours). This sample was an aliquot of the pH 7 solution
[b] 7 days storage at 40° C.
[c] 10 days storage at 40° C. followed by 7 days at 50° C.

TABLE 9 pH stability individual related substances assay for SPL026 in Britton-Robinson buffer, 7 days storage at 40° C.

| Nominal pH | Day[a] | \multicolumn{16}{c}{Relative retention time and percentage area of total peak area (peaks >0.05% of total peak area)} |
|---|---|---|---|---|---|---|---|---|---|---|---|---|---|---|---|---|---|
| | | 0.54 | 0.62 | 0.64 | 0.73 | 0.74 | 0.77 | 0.80 | 0.81 | 0.91 | 0.95 | 1.06 | 1.10 | 1.11 | 1.17 | 1.20 | 1.56 |
| 4 | 7 | — | — | — | — | — | — | — | — | — | — | — | — | — | — | — | — |
| 5 | 7 | — | — | — | — | — | — | — | — | — | — | — | — | — | — | — | — |
| 6 | 7 | — | — | — | — | — | — | — | — | — | — | — | — | — | — | — | — |
| 6.5 | 7 | — | — | — | — | — | — | — | — | — | — | — | — | — | — | — | — |
| 6.5 with N$_2$[a] | 7 | — | — | — | — | — | — | — | — | — | — | — | — | — | — | — | — |
| 7 UV light[b] | n/a[C] | 0.05 | 0.17 | 0.54 | 0.23 | 0.15 | 0.06 | 0.07 | — | — | — | — | — | — | 0.18 | 0.13 | 0.10 |
| 7 | 7 | — | — | — | — | — | — | — | — | — | — | — | — | — | — | — | — |
| 7.5 | 7 | — | — | — | — | — | — | — | — | — | — | — | — | — | — | — | — |
| 8 | 7 | — | — | — | — | — | — | — | — | — | — | — | — | — | — | — | — |
| 9 | 7 | — | — | — | — | — | — | — | — | — | — | — | — | — | — | — | — |

[a]Sparged with nitrogen
[b]UV light exposure (200 watt hours UVA, 0.6 million (μxhours)
[C]Subsample of the pH 7 formulation

TABLE 10 pH stability individual related substances assay for SPL026 in Britton-Robinson buffer, 10 days storage at 40° C., 7 days storage at 50° C.

| Nominal pH | Day[a] | \multicolumn{16}{c}{Relative retention time and percentage area of total peak area (peaks >0.05% of total peak area)} |
|---|---|---|---|---|---|---|---|---|---|---|---|---|---|---|---|---|---|
| | | 0.54 | 0.62 | 0.64 | 0.73 | 0.74 | 0.77 | 0.80 | 0.81 | 0.91 | 0.95 | 1.06 | 1.10 | 1.11 | 1.17 | 1.20 | 1.56 |
| 4 | 17 | — | — | — | — | — | — | — | — | — | — | — | — | — | — | — | — |
| 5 | 17 | — | — | — | — | — | — | — | — | — | — | — | — | — | — | — | 0.07 |
| 6 | 17 | — | — | — | — | — | — | — | — | — | — | — | — | — | — | — | 0.09 |
| 6.5 | 17 | — | — | — | — | — | — | — | — | — | — | — | — | — | — | — | 0.10 |
| 6.5 with N$_2$[a] | 17 | — | — | — | — | — | — | — | — | — | — | — | — | — | — | — | 0.05 |
| 7 | 17 | — | — | — | 0.09 | — | — | — | — | 0.05 | — | — | — | — | — | — | 0.12 |
| 7.5 | 17 | — | — | — | 0.14 | — | — | — | — | 0.07 | — | — | 0.12 | — | — | — | 0.09 |
| 8 | 17 | — | — | — | 0.15 | — | — | — | — | 0.09 | 0.05 | — | 0.22 | — | — | — | 0.07 |
| 9 | 17 | — | — | — | 0.12 | — | — | — | — | 0.11 | — | — | 0.12 | — | — | — | 0:38 |

[a]Sparged with nitrogen

Comparison of Stability of Initial Formulation with B-R Buffered Formulations

As described above, DMT fumarate formulations comprising the go-to buffer stored at temperatures of 40 to 50° C., without N$_2$ sparging or control of UV light exposure, contained 1.13% of related substances after 1 week of storage. The amounts of related substances that formed in the go-to formulation and the B-R formulations on storage for a week at 40 to 50° C. are compared in Table 11. DMT fumarate formulations comprising B-R buffers stored under the same conditions contained less than 0.02% of related substances after 1 week of storage (>5.7× fewer related substances than the go-to formulation) suggesting a greater stability of the B-R formulations.

As described above, when developing formulations for injection, it is typical to match the pH of the formulation with those of the patient's blood serum. Human blood serum has a pH of about 7.4. Consequently, the obvious go-to formulation of salts of optionally substituted dimethyltryptamine compounds is one with a pH of 7.4. A greater stability of formulations of such salts prepared at pH values of 7.0 or less was unexpected.

TABLE 11

Short-term formulation stability assessment of go-to formulation and formulations of the invention

| | pH | | Assay (mg/mL) | | Related Substances (%) | |
|---|---|---|---|---|---|---|
| Sample | Initial | Day 7 | Initial | Day 7 | Initial | Day 7 |
| 2.5 mg/mL/50 mM phosphate buffered saline, pH 7.4 (go-to formulation) | 6.88 | 6.87 | 2.49 | 2.38 | N.D <0.02 | 1.13 |
| 2.5 mg/mL/40 mM B-R buffer, pH 4.0 (non-obvious formulation) | 3.86 | 3.84 | 2.47 | 2.57 | N.D <0.02 | N.D <0.02 |
| 2.5 mg/mL/40 mM B-R buffer, pH 5.0 (non-obvious formulation) | 4.57 | 4.55 | 2.50 | 2.48 | N.D <0.02 | N.D <0.02 |

TABLE 11-continued

Short-term formulation stability assessment of go-to formulation and formulations of the invention

| Sample | pH Initial | pH Day 7 | Assay (mg/mL) Initial | Assay (mg/mL) Day 7 | Related Substances (%) Initial | Related Substances (%) Day 7 |
|---|---|---|---|---|---|---|
| 2.5 mg/mL/40 mM B-R buffer, pH 6.0 (non-obvious formulation) | 5.08 | 5.07 | 2.51 | 2.56 | N.D <0.02 | N.D <0.02 |
| 2.5 mg/mL/40 mM B-R buffer, pH 6.5 (non-obvious formulation) | 5.33 | 5.33 | 2.49 | 2.59 | N.D <0.02 | N.D <0.02 |
| 2.5 mg/mL/40 mM B-R buffer, pH 7.0 (non-obvious formulation) | 6.12 | 6.10 | 2.54 | 2.54 | N.D <0.02 | N.D <0.02 |

Candidate Formulation Development

From the results of the pH stability assessment the decision was made to fix the formulation pH at pH 4.0 (after storage for a week, the B-R formulation at pH 4.0 contained no peaks corresponding to related substances, suggesting that this was the most stable formulation) and to assess the use of phosphate and acetate buffer systems at concentrations of 20 mM and 40 mM, as these both buffer well at the optimal pH for stability, and assess both sodium chloride and dextrose as tonicity agents.

Formulation Preparation

Details of each individual formulation (numbered 1 to 8) are presented in Table 12 and Table 13. For each formulation, the requisite acid and tonicity agent was dissolved in 80 ml of water. The pH of this solution was then adjusted to pH 4 (+0.5) with 1 M sodium hydroxide solution. The drug substance was then dissolved, the pH adjusted to pH 4 (+0.1) with more 1 M sodium hydroxide solution and then made to volume with water and final pH check and adjusted as required. For each formulation, the volume of sodium hydroxide used was documented. The composition of each formulation is presented below in Table 12 (saline) and Table 13 (dextrose).

An aliquot of each formulation was taken for assay/ related substances and osmolality check. The remainder of each formulation was filtered (filter size 0.2 μm) into a clear glass multi-dose vial, sparged with nitrogen, capped and placed into storage (60° C.) for 14 days. The 40 mM phosphate/dextrose formulation (formulation 8) was split into two aliquots with one aliquot stored in an amber glass multi-dose vial and one aliquot in a clear glass multi-dose vial.

TABLE 12

Candidate SPL026 formulation preparations (saline)
Saline Formulations

| Ingredient | Formulation Number 1 | 2 | 3 | 4 |
|---|---|---|---|---|
| SPL026 | 398 mg | 398 mg | 398 mg | 398 mg |
| Acetic acid | 120 mg (20 mM) | 240 mg (40 mM) | — | — |
| Ortho-phosphoric acid (85%) | — | — | 231 mg (20 mM) | 461 mg (40 mM) |
| Sodium chloride | 780 mg | 720 mg | 780 mg | 720 mg |
| Sodium hydroxide | 38.8 mg | 60.8 mg | 103.2 mg | 185.6 mg |
| Volume prepared (mL) | 100 | 100 | 100 | 100 |

TABLE 13

Candidate SPL026 formulation preparations (dextrose)
Dextrose Formulations

| Ingredient | Formulation Number 5 | 6 | 7 | 8 |
|---|---|---|---|---|
| SPL026 | 398 mg | 398 mg | 398 mg | 398 mg |
| Acetic acid | 120 mg (20 mM) | 240 mg (40 mM) | — | — |
| Ortho-phosphoric acid (85%) | — | — | 231 mg (20 mM) | 461 mg (40 mM) |
| Dextrose | 4300 mg | 3900 mg | 4300 mg | 3900 mg |
| Sodium hydroxide | 27.6 | 47.2 | 96.4 mg | 175.2 mg |
| Volume prepared (mL) | 100 | 100 | 100 | 100 |

Results

Concentration, osmolality and pH results for formulations at preparation and following storage at 60° C. are presented in Table 14. Related substances results following storage are presented in Table 15.

All formulations on preparation were clear colourless solutions. No related substances were present in any of the formulations following preparation.

Following removal from storage all formulations in terms of their appearance were no longer colourless but had acquired to varying degrees a hint of beige but all remained clear, colour was most pronounced in formulation 5 (20 mM acetate buffer/dextrose) which had the greatest concentration of related substances.

Osmolality and pH were confirmed as stable for each tested formulation with no significant changes.

Total related substances as peaks of more than 0.05% of total peak area ranged between 0.07% up to 0.52%. These data would suggest that for SPL026 saline is the preferred tonicity agent over dextrose.

All Day 14 results for the 40 mM phosphate/dextrose formulation stored in amber glass mirrored the clear glass results confirming that clear glass/amber glass storage has no impact on stability in terms of these storage conditions but given the previously noted light instability amber glass should be used as the primary pack.

TABLE 14

Candidate SPL026 formulation results, assay, osmolality and pH

| No. | Vehicle composition | Concentration (mg · mL⁻¹) | | Osmolality (mOsm/kg) | | pH | |
|---|---|---|---|---|---|---|---|
| | | Day 0 | 14 days, 60° C. | Day 0 | 14 days, 60° C. | Day 0 | 14 days, 60° C. |
| 1 | 20 mM acetate/saline | 2.50 | 2.52 | 305 | 300 | 3.94 | 3.94 |
| 2 | 40 mM acetate/saline | 2.54 | 2.54 | 307 | 318 | 3.98 | 4.01 |
| 3 | 20 mM phosphate/saline | 2.55 | 2.54 | 315 | 319 | 4.01 | 4.02 |
| 4 | 40 mM phosphate/saline | 2.53 | 2.46 | 330 | 347 | 4.00 | 3.99 |
| 5 | 20 mM acetate/dextrose | 2.50 | 2.46 | 300 | 308 | 3.97 | 4.05 |
| 6 | 40 mM acetate/dextrose | 2.51 | 2.47 | 304 | 310 | 4.02 | 4.06 |
| 7 | 20 mM phosphate/dextrose | 2.55 | 2.51 | 320 | 320 | 4.02 | 4.04 |
| 8 | 40 mM phosphate/dextrose | 2.58 | 2.48 | 339 | 336 | 4.01 | 4.04 |
| 8[a] | 40 mM phosphate/dextrose | — | 2.49 | — | 334 | — | 4.02 |

[a]stored in amber glass

TABLE 15

Related substances assay for candidate SPL026 formulations following storage at 60° C. for 14 days

| | RRT and percentage area of total peak area of peaks >0.05% of total peak area | | | | | | |
|---|---|---|---|---|---|---|---|
| No. | 0.62 | 0.72 | 0.80 | 0.91 | 1.60 | 1.61 | Total |
| 1 | — | — | — | — | — | 0.11 | 0.11 |
| 2 | — | — | — | — | — | 0.08 | 0.08 |
| 3 | — | — | — | — | — | 0.09 | 0.09 |
| 4 | — | — | — | — | — | 0.07 | 0.07 |
| 5 | 0.05 | 0.05 | 0.07 | 0.07 | 0.08 | 0.20 | 0.52 |
| 6 | — | — | — | — | — | 0.13 | 0.13 |
| 7 | — | — | — | 0.05 | — | 0.16 | 0.21 |
| 8 | — | — | — | 0.05 | — | 0.15 | 0.20 |
| 8[a] | — | — | — | 0.07 | — | 0.23 | 0.30 |

[a]stored in amber glass

Conclusion

All the candidate formulations following the 14-day stability assessment were stable in terms of osmolality and pH. For formulations 1 to 3 there was no change in achieved concentration and for formulations 5-8 changes (losses on storage) were small (<0.1 mg·mL⁻¹). For each candidate formulation, related substances were very low at between 0.07 to 0.52% of the total peak area. More related substances were observed in the dextrose formulations than in the saline formulations.

Following review of the data the following SPL026 formulation was chosen (herein referred to as SPL026 formulation 10). This is based on formulation 1 but the acetate buffer content is increased slightly to ensure robust buffering in the formulation over the shelf life but at a low enough level to ensure that blood buffering effects are minimal. Sodium chloride levels were dropped slightly to compensate for the additional acetate but to maintain an iso-osmotic solution. This formulation was prepared and analysed for assay, pH and osmolality on preparation. Preparation details and achieved results are presented below in Table 16.

TABLE 16

SPL026, 2.5 mg/mL formulation 10 preparation and results

| Preparation | SPL026 | 398 mg* |
|---|---|---|
| | Acetic acid | 150 mg |
| | Sodium chloride | 760 mg |
| | Sodium hydroxide | q.s. to pH 4.0 ≈ 40 mg |

TABLE 16-continued

SPL026, 2.5 mg/mL formulation 10 preparation and results

| Result | Volume prepared (mL) | 100 |
|---|---|---|
| | Appearance | Clear colourless solution |
| | Osmolality (mOsm/kg) | 299 |
| | pH | 3.96 |
| | Assay (mg.mL⁻¹) | 2.49 |

*398 mg SPL026 (DMT fumarate) is equivalent to 250 mg of free base (DMT)

Recommended Process Overview for Formulation Preparation (Batch Size 100 mL)
Preparation of Vehicles
Preparation of 1M Sodium Hydroxide Solution (100 mL)
1) Weigh 4 g of sodium hydroxide pellets into a suitably sized beaker.
2) Dispense 80 ml of Water for injection (WFI) water into the beaker.
3) Magnetically stir to achieve dissolution and allow the solution to cool to laboratory temperature.
4) Add purified water to make up to 100 mL.
5) Transfer into a type 1 borosilicate glass container.
Preparation of Formulation 10 (2.5 mg/mL)
1) Accurately weigh 760 mg of sodium chloride into a suitable container
2) Weigh by difference the required amount of drug substance into a suitable container (glass weigh boat). Ensure that mass of drug substance taken includes correction for salt and purity.
3) Carefully transfer the weighed drug substance into a beaker. Rinse out the weighing container with WFI ensuring no solids remain. Add further WFI to the drug substance up to ¾ of the required total volume and magnetically stir to dissolve. Add batch quantity of acetic acid (note acetic acid is volatile and so this step must be performed immediately after weighing).
4) Add the pre-weighed sodium chloride.
5) Once dissolution is complete, adjust the pH of the formulation to pH 4 (±0.1) with dropwise addition of the freshly prepared 1M sodium hydroxide solution whilst continually stirring.
6) Make to volume in a suitable container and lastly check the pH is pH 4 (±0.1) and adjust if required.
7) The drug product solution is clear with a very slight hint of a beige colour. This colour is removed on filtration (step 6) to leave a colourless solution filtration.

8) Bubble nitrogen through the formulation until the measured dissolved oxygen content is below 2 ppm.
9) Syringe filter the solution either 0.22 μm or 0.2 μm into an amber glass multi-dose vial.

Below, reference is made to both technical and clinical batches of Formulation 10. Each of these have identical composition, but the technical batch was not made to GMP.

Stability of Formulation 10 (Technical Batch)

Appearance and pH

Appearance and pH results for formulation 10 (technical batch) at preparation and following storage at 2-8° C., 25° C./60% relative humidity (RH) and 40°/75% RH are presented in Table 17. At T=0 (the initial analysis), the pH met the specification of 3.8-4.2 and the osmolality met the specification of 270-330 mOsm/kg (296 mOsm/kg). By T=9 months, there are no significant changes in appearance on storage at 2-8° C. or at 25° C./60% RH. However, at 40° C./75% RH there is an obvious colour change in the product at T=6 months. There was an indication of colour change at the 2 and 3 month points on storage at 40° C./75% RH when compared to the other storage conditions, but at 6 months the colour change was obvious. There was no change in pH by the 9 month time point on storage at 2-8° C. or 25° C./60% RH or by the 6 month time point on storage at 40° C./75% RH.

TABLE 17

Appearance and pH of formulation 10 after storage under the conditions specified

| Time-point/months | | Appearance | pH |
|---|---|---|---|
| Initial (T = 0) | | Clear colourless liquid, free from visible particulates | 4.0 |
| 2-8° C. | T = 1 | Clear colourless liquid, free from visible particulates | 4.0 |
| | T = 2 | Clear colourless liquid, free from visible particulates | 4.0 |
| | T = 3 | Clear colourless liquid, free from visible particulates | 4.0 |
| | T = 6 | Clear colourless liquid, free from visible particulates | 4.0 |
| | T = 9 | Clear colourless liquid, free from visible particulates | 4.0 |
| 25° C./ 60% RH | T = 1 | Clear colourless liquid, free from visible particulates | 4.0 |
| | T = 2 | Clear colourless liquid, free from visible particulates | 4.0 |
| | T = 3 | Clear colourless liquid, free from visible particulates | 4.0 |
| | T = 6 | Clear colourless liquid, free from visible particulates | 4.0 |
| | T = 9 | Clear colourless liquid, free from visible particulates[1] | 4.0 |
| 40° C./ 75% RH | T = 1 | Clear colourless liquid, free from visible particulates | 4.0 |
| | T = 2 | Clear colourless liquid, free from visible particulates | 4.0 |
| | T = 3 | Clear colourless liquid, free from visible particulates | 4.0 |
| | T = 6 | Clear light yellow liquid, free from visible particulates | 4.0 |

Sub-Visible Particulates

The number of sub-visible particles within formulation 10 (technical batch) at preparation and following storage at 2-8° C., 25° C./60% relative humidity (RH) and 40°/75% RH is presented in Table 18. After 6 months storage at 2-8° C., 25° C./60% RH and 40° C./75% RH there is no significant change in sub-visible particulates (see Table 18).

TABLE 18

Sub-visible particulates of formulation 10 after storage under the conditions specified

| Time-point/months | | Count/vial[1] | | Pass/fail[2] |
|---|---|---|---|---|
| | | ≥10 um | ≥25 um | |
| Initial (T = 0) | | 5 | 1 | Pass |
| 5° C. | T = 6 | 3 | 0 | Pass |
| 25° C./60% RH | T = 1 | 9 | 0 | Pass |
| | T = 6 | 3 | 0 | Pass |
| 40° C./75% RH | T = 1 | 4 | 0 | Pass |
| | T = 6 | 14 | 1 | Pass |

[1]Where fill volume is 10.5 mL
[2]Number particles with diameter ≥ 10 μm per vial <6000 = PASS and number particles with diameter ≥ 25 μm per vial <600 = PASS Extractable Volume The extractable volume from 6 vials of formulation 10 (technical batch) is presented in Table 19. The density used to calculate the volume was taken from the placebo data used in batch manufacture (1.008 g/cm$^3$). The extractable volume meets the specification of NLT 10.0 mL.

TABLE 19

Extractable volume of formulation 10

| Sample | Sample weight (g) | Extractable volume (mL) |
|---|---|---|
| 1 | 10.2791 | 10.1975 |
| 2 | 10.4192 | 10.3365 |
| 3 | 10.2732 | 10.1917 |
| 4 | 10.3162 | 10.2343 |
| 5 | 10.2696 | 10.1881 |
| 6 | 10.2516 | 10.1702 |
| Mean | 10.3 | 10.2 |

Percentage Recovery

The percentage recovery of SPL026 (free base, mg/mL) within formulation 10 (technical batch) at preparation and following storage at 2-8° C., 25° C./60% relative humidity (RH) and 40°/75% RH is presented in Table 20. There were no significant changes in the purity of the formulation after 9 months storage at 2-8° C. or 25° C./60% RH and 6 months storage at 40° C./75% RH. All recoveries versus the theoretical concentration and T=0 are within the specification of 90.0-105.0%

TABLE 20

Percentage recovery of SPL026 from formulation 10 after storage under the conditions specified

| | Time-point/months | | 1 | 2 | Mean | Rec./theory[1] (%) | Rec./T = 0[2] (%) |
|---|---|---|---|---|---|---|---|
| | Pre-filtration | | 2.518 | 2.506 | 2.51 | 100.5 | — |
| | Post-filtration | | 2.516 | 2.504 | 2.51 | 100.4 | 99.9[3] |
| | Initial (T = 0) | | 2.503 | 2.501 | 2.50 | 100.1 | — |
| 5° C. | | T = 1 | 2.508 | 2.508 | 2.51 | 100.2 | 100.3 |
| | | T = 2 | 2.538 | 2.539 | 2.54 | 101.5 | 101.5 |
| | | T = 3 | 2.512 | 2.523 | 2.52 | 100.8 | 100.7 |
| | | T = 6 | 2.515 | 2.525 | 2.52 | 100.8 | 100.7 |
| | | T = 9 | 2.511 | 2.504 | 2.51 | 100.3 | 100.2 |

TABLE 20-continued

Percentage recovery of SPL026 from formulation 10 after storage under the conditions specified

| Time-point/months | | 1 | 2 | Mean | Rec./theory[1] (%) | Rec./T = 0[2] (%) |
|---|---|---|---|---|---|---|
| 25° C./60% RH | T = 1 | 2.508 | 2.509 | 2.51 | 100.3 | 100.3 |
| | T = 2 | 2.541 | 2.535 | 2.54 | 101.5 | 101.4 |
| | T = 3 | 2.525 | 2.524 | 2.52 | 101.0 | 100.9 |
| | T = 6 | 2.497 | 2.525 | 2.51 | 100.4 | 100.4 |
| | T = 9 | 2.475 | 2.496 | 2.49 | 99.4 | 99.3 |
| 40° C./75% RH | T = 1 | 2.510 | 2.499 | 2.50 | 100.1 | 100.2 |
| | T = 2 | 2.538 | 2.536 | 2.54 | 101.5 | 101.4 |
| | T = 3 | 2.505 | 2.501 | 2.50 | 100.1 | 100.0 |
| | T = 6 | 2.494 | 2.494 | 2.49 | 99.8 | 99.7 |

[1] As percentage of theoretical 2.5 mg/mL.
[2] As percentage of initial (T = 0) result.
[3] As percentage of pre-filtration result.

Purity/Related Substances

The purity of SPL026 (free base, mg/mL) and the amount of impurities observed at different retention times within formulation 10 (technical batch) at preparation and following storage at 2-8° C., 25° C./60% relative humidity (RH) and 40°/75% RH are presented in Table 21, Table 22 and Table 23, respectively. The total impurities observed in formulations after 9 months storage at 2-8° C. and 25° C./60% RH have increased slightly due to the impurity at RRT 1.04 being observed for the first time and above the LOQ limit at both conditions. Increases in total impurities were noted for the sample stored at 40° C./75% RH from 2 months. An increase in the impurity observed at RRT 1.60 is noted from T=2 months at 40° C./75% RH in comparison to the other storage conditions, which may be attributed to the higher storage temperature of 40° C.

TABLE 21

Purity/related substances of SPL026 from formulation 10 after storage at 2-8° C.

| | Time-point/months and amount (% w/w) | | | | | |
|---|---|---|---|---|---|---|
| RRT | Initial (T = 0) | 1 | 2 | 3 | 6 | 9 |
| SPL026 (free base)[1] | 100.0 | 100.0 | 100.0 | 100.0 | 100.0 | 100.0 (99.95) |
| 1.04 | ND | ND | ND | ND | ND | 0.05 |
| 1.60 | ND | ND | <LOQ | <LOQ | <LOQ | <LOQ |
| Total[2] | ND | ND | <LOQ | <LOQ | <LOQ | 0.05 |

[1] SPL026 purity calculated as 100 – total related substances.
[2] Sum of related substances ≥ 0.05%

TABLE 22

Purity/related substances of SPL026 from formulation 10 after storage at 25° C./60% RH

| | Time-point/months and amount (% w/w) | | | | | |
|---|---|---|---|---|---|---|
| RRT | Initial (T = 0) | 1 | 2 | 3 | 6 | 9 |
| SPL026 (free base)[1] | 100.0 | 100.0 | 100.0 | 100.0 | 100.0 | 100.0 (99.95) |
| 1.04 | ND | ND | ND | ND | ND | 0.05 |
| 1.18 | ND | ND | <LOQ | ND | ND | ND |
| 1.60 | ND | ND | <LOQ | <LOQ | <LOQ | <LOQ |
| Total[2] | ND | ND | <LOQ | <LOQ | <LOQ | 0.05 |

[1] SPL026 purity calculated as 100 – total related substances.
[2] Sum of related substances ≥ 0.05%

TABLE 23

Purity/related substances of SPL026 from formulation 10 after storage at 40° C./75% RH

| RRT | Time-point/months and amount (% w/w) | | | | |
|---|---|---|---|---|---|
| | Initial (T = 0) | 1 | 2 | 3 | 6 |
| 0.49 | ND | ND | ND | ND | 0.05 |
| 0.70 | ND | ND | <LOQ | <LOQ | 0.05 |
| 0.77 | ND | ND | ND | <LOQ | <LOQ |
| 0.81 | ND | ND | <LOQ | <LOQ | 0.05 |
| 0.92 | ND | ND | <LOQ | <LOQ | 0.06 |
| SPL026 (free base) [1] | 100.0 | 100.0 | 99.9 | 99.9 | 99.7 |
| 1.19 | ND | ND | ND | ND | <LOQ |
| 1.22 | ND | ND | ND | ND | <LOQ |
| 1.60 | ND | ND | 0.05 | 0.07 | 0.10 |
| Total[2] | ND | ND | 0.05 | 0.07 | 0.31 |

[1] SPL026 purity calculated as 100 − total related substances.
[2] Sum of related substances ≥ 0.05%

Stability of Formulation 10 (Clinical Batch)

At T=0 (the initial analysis), the pH met the specification of 3.8-4.2, the osmolality met the specification of 270-330 mOsm/kg (being 306 mOsm/kg), and the extractable volume met the NLT of 10.0 mL (being 10.4 mL). In addition, at T=0, the number of sub visible particulates was 4 particles/vial of a size ≥10 μm and 0 particles/vial of a size ≥25 μm, which is well within the specification of not more than 6000 particles/vial of a size ≥10 μm and not more than 600 particles/vial of a size ≥25 μm. At T=0, the UV-vis spectrum of the formulation conformed to reference spectra ($\lambda^{max}$ at 221±3 nm and 279±3 nm), and the signal was observed at +2% retention time of the reference standard. Finally, at T=0, container closure integrity testing showed no dye ingress, and the formulation was sterile, comprising <0.01 EU/mL of bacterial endotoxins, which is well within the specification of 20.5 EU/mL.

Appearance and pH

Appearance and pH results for formulation 10 (clinical batch) at preparation and following storage at 2-8° C., 25° C./60% relative humidity (RH) and 40°/75% RH are presented in Table 24. By T=3 months, there are no significant changes in appearance on storage at 2-8° C., at 25° C./60% RH or at 40° C./75% RH. There was an indication of colour change at the 3 month point. There was no change in pH.

TABLE 24

Appearance and pH of formulation 10 after storage under the conditions specified

| Time-point/months | | Appearance | pH |
|---|---|---|---|
| Initial (T = 0) | | Clear colourless liquid, practically free from particulates | 4.0 |
| 2-8° C. | T = 1 | Clear colourless liquid, practically free from particulates | 3.9 |
| | T = 3 | Clear pale yellow liquid, practically free from particulates | 4.0 |
| 25° C./60% RH | T = 1 | Clear colourless liquid, practically free from particulates | 4.0 |
| | T = 3 | Clear pale yellow liquid, practically free from particulates | 4.0 |
| 40° C./75% RH | T = 1 | Clear colourless liquid, practically free from particulates | 3.9 |
| | T = 3 | Clear pale yellow liquid, practically free from particulates | 4.0 |

Percentage Recovery

The percentage recovery of SPL026 (free base, mg/mL) within formulation 10 (clinical batch) at preparation and following storage at 2-8° C., 25° C./60% relative humidity (RH) and 40°/75% RH is presented in Table 25. There were no significant changes in the purity of the formulation after 3 months storage at 2-8° C. or 25° C./60% RH and 40° C./75% RH. All recoveries versus the theoretical concentration and T=0 are within the specification of 95.0-105.0%

TABLE 25

Percentage recovery of SPL026 from formulation 10 after storage under the conditions specified

| Time-point/months | | Percentage recover of SPL026 (%) |
|---|---|---|
| Initial (T = 0) | | 103.6 |
| 2-8° C. | T = 1 | 102.9 |
| | T = 3 | 103.2 |
| 25° C./60% RH | T = 1 | 102.7 |
| | T = 3 | 103.0 |
| 40° C./75% RH | T = 1 | 102.6 |
| | T = 3 | 102.5 |

Purity/Related Substances

The purity of SPL026 (free base, mg/mL) and the amount of impurities observed at different retention times within formulation 10 (clinical batch) at preparation and following storage at 2-8° C., 25° C./60% relative humidity (RH) and 40°/75% RH are presented in Table 26, Table 27 and Table 28, respectively.

TABLE 26

Purity/related substances of SPL026 from formulation 10 after storage at 2-8° C.

| RRT | Time-point/months and amount (Area %) | | |
|---|---|---|---|
| | Initial (T = 0) | 1 | 3 |
| 1.11 | <LOQ | <LOQ | <LOQ |
| 1.59-1.60 | 0.07 | 0.08 | 0.07 |
| Total[2] | 0.07 | 0.08 | 0.07 |

[2] Sum of related substances ≥ 0.05%

TABLE 27

Purity/related substances of SPL026 from formulation 10 after storage at 25° C./60% RH

| RRT | Time-point/months and amount (Area %) | | |
|---|---|---|---|
| | Initial (T = 0) | 1 | 3 |
| 1.11 | <LOQ | <LOQ | <LOQ |
| 1.59-1.60 | 0.07 | 0.08 | 0.07 |
| Total[2] | 0.07 | 0.08 | 0.07 |

[2] Sum of related substances ≥ 0.05%

TABLE 28

Purity/related substances of SPL026 from formulation 10 after storage at 40° C./75% RH

| RRT | Time-point/months and amount (Area %) | | |
|---|---|---|---|
| | Initial (T = 0) | 1 | 3 |
| 0.56 | <LOQ | <LOQ | <LOQ |
| 0.70 | <LOQ | <LOQ | <LOQ |
| 0.82 | <LOQ | <LOQ | <LOQ |
| 0.94 | <LOQ | <LOQ | <LOQ |
| 1.11 | <LOQ | <LOQ | <LOQ |
| 1.59-1.60 | 0.07 | 0.08 | 0.09 |
| Total[2] | 0.07 | 0.08 | 0.09 |

[2] Sum of related substances ≥ 0.05%

The invention claimed is:

1. A pharmaceutical formulation suitable for injection, comprising:
   a salt of a dimethyltryptamine compound which is substituted with deuterium at one or more positions selected from the α, β and dimethyl carbon atoms;
   a buffer which is separate to the salt; and
   water,
   wherein the formulation has a pH of about 3.5 to about 6.5 and an osmolality of about 250 mOsm/Kg to about 350 mOsm/Kg, and
   wherein the formulation has an oxygen content of less than 2 ppm.

2. The formulation of claim 1, wherein the dimethyltryptamine compound is a compound of Formula I:

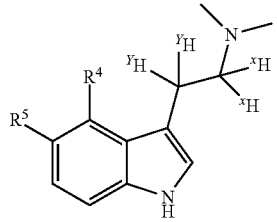

Formula I wherein:
   $R^4$ and $R^5$ are both H; and
   each $^XH$ and each $^YH$ is independently selected from H and D,
   wherein at least one of $^XH$ and each $^YH$ is D.

3. The formulation of claim 1, comprising any one of or a combination of α-monodeutero-N,N-dimethyltryptamine, α,α-dideutero-N,N-dimethyltryptamine, α,β-dideutero-N,N-dimethyltryptamine, α,α,β-trideutero-N,N-dimethyltryptamine, α,β,β-trideutero-N,N-dimethyltryptamine and α,α,β,β-tetradeutero-N,N-dimethyltryptamine.

4. The formulation of claim 3, wherein the formulation comprises α,α-dideutero-N,N-dimethyltryptamine.

5. The formulation of claim 3, wherein the formulation comprises α-monodeutero-N,N-dimethyltryptamine.

6. The formulation of claim 3, wherein the formulation comprises α,α-dideutero-N,N-dimethyltryptamine and α-monodeutero-N,N-dimethyltryptamine.

7. The formulation of claim 1, wherein the dimethyltryptamine compound is substituted with deuterium at one or more positions on the dimethyl carbon atoms.

8. The formulation of claim 7, wherein the dimethyltryptamine compound is substituted with deuterium at all positions on the dimethyl carbon atoms.

9. The formulation of claim 7, wherein the dimethyltryptamine compound is substituted with deuterium at one or more positions on the dimethyl carbon atoms and at one or both α-carbon positions.

10. The formulation of claim 7, wherein the dimethyltryptamine compound is substituted with deuterium at one or more positions on the dimethyl carbon atoms, at one or both α-carbon positions (α-monodeutero or α,α-dideutero), and at one or both β-carbon positions (β-monodeutero or β,β-dideutero).

11. The formulation of claim 10, wherein the dimethyltryptamine compound is substituted with deuterium at all positions on the dimethyl carbon atoms and at one or both α-carbon positions.

12. The formulation of claim 11, wherein the dimethyltryptamine compound is substituted with deuterium at all positions on the dimethyl carbon atoms and at both α-carbon positions.

13. The formulation of claim 12, wherein the dimethyltryptamine compound is substituted with deuterium at all positions on the dimethyl carbon atoms, at both α-carbon positions, and at both β-carbon positions.

14. The formulation of claim 1, wherein the pH is from about 3.75 to about 6.5.

15. The formulation of claim 14, wherein the pH is from about 3.75 to about 5.75.

16. The formulation of claim 1, wherein the pH is from about 3.75 to about 4.25.

17. The formulation of claim 1, wherein the formulation has an osmolality of about 275 to about 325 mOsm/Kg.

18. The formulation of claim 1, wherein the salt is of a deuterium-substituted dimethyltryptamine compound and an acid selected from the group consisting of fumaric acid, tartaric acid, citric acid, acetic acid, lactic acid and gluconic acid.

19. The formulation of claim 18, wherein the acid is fumaric acid.

* * * * *